(12) United States Patent
Sackinger et al.

(10) Patent No.: US 9,198,995 B2
(45) Date of Patent: Dec. 1, 2015

(54) CONFORMABLE STRUCTURED THERAPEUTIC DRESSING

(75) Inventors: Scott Thomas Sackinger, Sherwood, OR (US); Matthew Alan Warren, Salem, OR (US)

(73) Assignee: Ore-Medix LLC, Lebanon, OR (US)

( * ) Notice: Subject to any disclaimer, the term of this patent is extended or adjusted under 35 U.S.C. 154(b) by 561 days.

(21) Appl. No.: 12/442,099

(22) PCT Filed: Sep. 17, 2007

(86) PCT No.: PCT/US2007/020110
§ 371 (c)(1),
(2), (4) Date: Mar. 19, 2009

(87) PCT Pub. No.: WO2008/036225
PCT Pub. Date: Mar. 27, 2008

(65) Prior Publication Data
US 2010/0021528 A1  Jan. 28, 2010

Related U.S. Application Data

(60) Provisional application No. 60/846,212, filed on Sep. 20, 2006, provisional application No. 60/946,355, filed on Jun. 26, 2007.

(51) Int. Cl.
*A61K 9/00* (2006.01)
*A61K 31/722* (2006.01)
(Continued)

(52) U.S. Cl.
CPC .................. *A61L 15/18* (2013.01); *A61L 15/28* (2013.01); *A61L 15/425* (2013.01); *A61L 15/44* (2013.01); *A61L 2300/418* (2013.01)

(58) Field of Classification Search
CPC .................................................... A61L 15/425
See application file for complete search history.

(56) References Cited

U.S. PATENT DOCUMENTS 3,903,268 A 9/1975 Balassa
4,543,410 A 9/1985 Cruz, Jr.
(Continued)

FOREIGN PATENT DOCUMENTS

WO     WO 00/09176      2/2000
WO   WO 2004/060172 A1    7/2004
(Continued)

OTHER PUBLICATIONS

Ralph K. Iler, "The Chemistry of Silica," John Wiley & Sons, pp. 761-767.
(Continued)

*Primary Examiner* — Scott Long
*Assistant Examiner* — Sarah Alawadi
(74) *Attorney, Agent, or Firm* — Stoel Rives LLP

(57) ABSTRACT

A conformable structured therapeutic dressing (120) has maximum available surface area (102) of a therapeutic agent (122) to stimulate therapeutic response in wounded tissue of a mammalian subject. In preferred embodiments, the therapeutic agent includes a procoagulant to quickly arrest bleeding and prevent life-threatening blood loss. The wound dressing exhibits a structured adsorbent (104) that maximizes available surface area of a functional filler (72). This is achieved with a minimal amount of binder (82) and small, porous particles of the functional filler. Minimizing the binder maximizes the amount of functional filler and reduces the chance that the binder will block access to the surface area of the functional filler. Porous particles have a large internal surface area. Structured adsorbents with higher surface areas, higher inter- and intra-fiber porosities, and low internal mass transfer resistances produce higher rates of mass transfer of an adsorbent onto the functional filler.

27 Claims, 27 Drawing Sheets

(51) Int. Cl.
| | |
|---|---|
| *A61K 33/00* | (2006.01) |
| *A61K 33/12* | (2006.01) |
| *A61K 31/76* | (2006.01) |
| *A61K 31/785* | (2006.01) |
| *A61K 31/765* | (2006.01) |
| *A61P 17/02* | (2006.01) |
| *A61P 13/00* | (2006.01) |
| *A61P 7/04* | (2006.01) |
| *A61L 15/18* | (2006.01) |
| *A61L 15/28* | (2006.01) |
| *A61L 15/42* | (2006.01) |
| *A61L 15/44* | (2006.01) |

(56) References Cited

U.S. PATENT DOCUMENTS

| | | | |
|---|---|---|---|
| 4,572,906 A | 2/1986 | Sparkes et al. | |
| 4,748,978 A | 6/1988 | Kamp | |
| 5,093,197 A | 3/1992 | Howard et al. | |
| 5,126,219 A | 6/1992 | Howard et al. | |
| 5,230,843 A | 7/1993 | Howard et al. | |
| 5,230,949 A | 7/1993 | Howard et al. | |
| 5,876,855 A * | 3/1999 | Wong et al. | 428/355 BL |
| 5,900,479 A | 5/1999 | Glasser et al. | |
| 5,955,422 A | 9/1999 | Lin | |
| 5,993,661 A | 11/1999 | Ruckenstein et al. | |
| 6,060,461 A | 5/2000 | Drake | |
| 6,379,712 B1 | 4/2002 | Yan et al. | |
| 6,720,006 B2 | 4/2004 | Hanke et al. | |
| 6,762,336 B1 | 7/2004 | MacPhee et al. | |
| 6,855,860 B2 | 2/2005 | Ruszczak et al. | |
| 6,891,077 B2 | 5/2005 | Rothwell et al. | |
| 6,897,348 B2 | 5/2005 | Malik | |
| 7,141,714 B2 | 11/2006 | Nielsen | |
| 2003/0133990 A1 * | 7/2003 | Hursey et al. | 424/601 |
| 2004/0241436 A1 * | 12/2004 | Hsieh et al. | 428/361 |
| 2004/0243043 A1 * | 12/2004 | McCarthy et al. | 602/46 |
| 2005/0038369 A1 * | 2/2005 | Gregory et al. | 602/48 |
| 2005/0125036 A1 * | 6/2005 | Roby | 606/228 |
| 2005/0137512 A1 | 6/2005 | Campbell et al. | |
| 2005/0147656 A1 | 7/2005 | McCarthy et al. | |
| 2006/0004314 A1 | 1/2006 | McCarthy et al. | |
| 2006/0034935 A1 * | 2/2006 | Pronovost et al. | 424/489 |
| 2006/0094320 A1 * | 5/2006 | Chen et al. | 442/340 |
| 2007/0154509 A1 | 7/2007 | Wilcher et al. | |
| 2007/0154510 A1 | 7/2007 | Wilcher et al. | |
| 2007/0154564 A1 | 7/2007 | Stucky et al. | |
| 2007/0275073 A1 * | 11/2007 | Huey et al. | 424/489 |

FOREIGN PATENT DOCUMENTS

| | | |
|---|---|---|
| WO | WO 2005/027808 A1 | 3/2005 |
| WO | WO 2005/062889 A2 | 7/2005 |
| WO | WO 2005/062896 A3 | 7/2005 |
| WO | WO 2006/088912 A2 | 8/2006 |
| WO | WO 2007/120342 | 10/2007 |

OTHER PUBLICATIONS

Lawrence L. K. Leung, M.D., Hemostatis and its Regulation, *ACP Medicine, Hematology: XII*, Jun. 2003 update, 10 pages.

Hyun Suk Whang et al., Hemostatic Agents Derived from Chitin and Chitosan, *Journal of Macromolecular Science, Part C: Polymer Reviews*, vol. 45, 2005, pp. 309-323.

Galen D. Stucky et al., Oxide Hemostatic Activity, *Journal of the American Chemical Society*, vol. 128, Issue 26, Jul. 5, 2006, pp. 8384-8385.

Martin A. Schreiber, M.D., et al., The Effect of Recombinant Factor VIIa on Coagulopathic Pigs with Grade V Liver Injuries, *The Journal of TRAUMA Injury, Infection, and Critical Care*, Aug. 2002, 53:252-259.

* cited by examiner

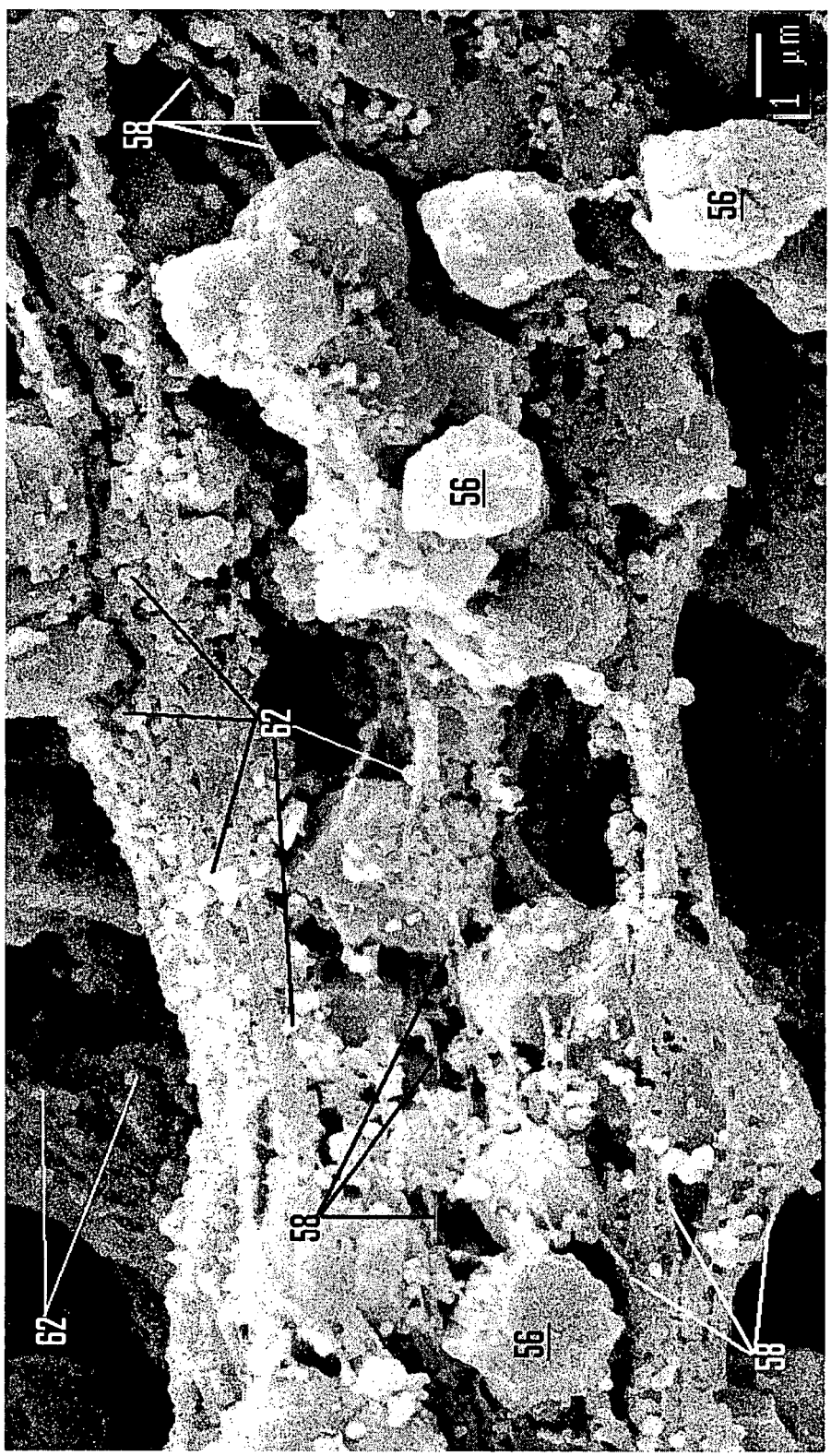

CONFORMABLE STRUCTURED THERAPEUTIC DRESSING

RELATED APPLICATIONS

This application is a 371 of International Application No. PCT/US07/20110, filed Sep. 17, 2007, which claims benefit of U.S. Provisional Patent Application Nos. 60/846,212 and 60/946,355, filed Sep. 20, 2006 and Jun. 26, 2007, respectively.

COPYRIGHT NOTICE

©2007 Entek Manufacturing, Inc. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71(d).

TECHNICAL FIELD

The present disclosure relates generally to articles of filled polymeric fibers and, in particular, to articles made from porous fibers that contain or are treated with procoagulant or therapeutic agents. These articles are useful as dressings for hemorrhage control and healing of a wound site in a mammalian subject. The articles have an unusually high percentage of functional fillers and very large surface areas. These properties, coupled with the selection of appropriate functional fillers, increase the efficacy of the disclosed articles compared to that of prior art in the field.

BACKGROUND INFORMATION

Composite polymer materials are made by the addition of functional fillers or additives to polymer materials. Compared to unfilled polymers, composites typically have a lower cost and/or improved physical properties. Functional fillers can be melt processed with the polymers or, following extrusion, impregnated into, suffused onto, or coated onto fibers or films either during fabrication or as a post-treatment. Typically the amount of functional filler that can be impregnated, suffused, or coated is limited by undesirable changes in mechanical properties, cost, and/or excessive shedding of the filler.

Filtration systems for liquids and gases are examples of one application of composite polymer materials. Economical, effective fluid filtration is accomplished by functional fillers that are supported and are not allowed to shed into the filtrate stream. Functional fillers used for filtration include activated carbon, zeolites, and catalysts. Structured adsorbents incorporate functional fillers into a fabric-like or porous solid structure. These articles typically are composed of a binder and functional fillers. Care is taken when designing structured adsorbents to select the fillers and optimize the structure of the adsorbent to achieve the desired rate and capacity of adsorbance.

FIGS. 1A and 1B show, respectively, AQF™ and KX™ adsorptive filtration media of structured activated carbon. FIG. 1A shows AQF™ air filtration media 10 that includes two-component fibers 12 and activated carbon granules 14. Fibers 12 have an inner core made from one polymer and an outer surface made from a second polymer. The polymer on the outer surface has a lower melting temperature than that of the polymer used for the inner core. Fibers 12 are heated to soften the outer surface, and then powders such as activated carbon granules 14 are blown onto the fibers. The softened polymer on the fiber surface acts as an adhesive. Activated carbon granules 14 can be partly covered or blinded by the adhesive, and is not incorporated within a fiber. The loss of active surface on the filler material that results from the adhesive blinding the filler reduces the adsorption capacity. The relatively large particle size required increases mass transfer resistance because adsorption needs to take place inside the particle, rather than on the surface. This results in slower kinetics compared to the kinetics of a material with smaller particles and less blinding of active surface area. In the example shown in FIG. 1B, KX™ PLEXX™ water filtration media 20 include fibers 22 having surfaces to which activated carbon granules 24 are adhered by a binder material 26. Activated carbon granules 24 are trapped by a web of fibers. The structure of this material limits the rate and capacity of adsorption and exhibits limiting issues that are similar to those discussed above in the AQF™ media case.

FIG. 2 presents another example of current approaches to impregnating fabrics and filter media with granular activated carbon. FIG. 2 is a SEM image of Lydall water filtration media 30 having a randomly configured fibrous substrate. Activated carbon granules 34 adhere to the surfaces of fibers 36. As in the KX™ and AQF™ media examples, fibers 36 of the substrate are composed of polymer.

Chitosan, together with its derivatives (e.g., chitosan acetate or chitosan lactate), is reported to possess hemostatic and antimicrobial properties and has been incorporated into bandages as a procoagulant to arrest bleeding. Publications concerning hemostasis discuss different aspects of blood clotting and their mechanisms. A review article, Whank, Hyun Suk et al. *Journal of Macromolecular Science*, Part C: Polymer Reviews, 45:309-323, 2005, discusses the role of chitosan and chitosan derivatives in platelet adhesion and platelet aggregation leading to clot formation. Platelet adhesion and platelet aggregation are aspects of cellular mechanisms for mammalian blood clotting. Chitosan is a de-acetylated product of chitin $(C_8H_{13}NO_5)_n$, an abundant natural glucosamine polysaccharide occurring in the shells of crustaceans, such as crabs, lobsters, and shrimp. Chitosan is non-toxic and biodegradable.

U.S. Pat. No. 3,903,268 discusses impregnating surgical gauze or pads with a solution of chitin or chitin derivatives and applying fibers composed of chitin and chitin derivatives to a wound to promote healing. U.S. Pat. No. 5,900,479 discusses the preparation of chitosan solutions in the form of chitosonium ion complexes or chitosan salts that can be formed into fibers and other shapes as an intermediate step, and then heated to achieve a polyanionic polymer condensation reaction. A characteristic of this formulation is that condensed chitosan salts resist dissolution in aqueous solutions. U.S. Pat. No. 6,897,348 describes a multi-layered bandage in which hemostatic agents, such as chitosan, and antimicrobial agents are present either within or as a coating over one of the bandage layers. Chitin fibers are pulverized and either incorporated into a woven substrate or applied in powder form directly to the wound. U.S. Pat. No. 4,543,410 describes the incorporation of chitin derivatives into a cellulose sponge to form a hemostatic material. U.S. Pat. No. 4,572,906 describes a solution of chitosan and lactic acid mixed with gelatin to form a wound-adherent hemostatic film. In all of the articles described by these patents, the surface areas of the healing agents presented to the wound are limited to the coating of the agents applied to the surfaces of the supporting fibers.

U.S. Patent Application Pub. No. US2005/0137512 describes a wound dressing for controlling severe bleeding. The wound dressing is prepared by degassing a chitosan biomaterial solution by heating at vacuum pressure, freezing the chitosan biomaterial solution, removing water from within the frozen chitosan biomaterial by freeze drying, compressing the chitosan biomaterial to obtain a compressed sponge, and baking the compressed chitosan sponge at 80° C. for 30 minutes. The resulting article is substantially comprised of the active ingredient chitosan. The compressed chitosan sponge is brittle and tends to crack if wrapped around a curved body part of a patient, making it impractical for use as a bandage in some situations. Also, the article works best when there is dry or slightly moist tissue around the wound area because the article adheres to these areas. The article is difficult to apply successfully to an internal wound or to a severe and/or irregular shaped external wound. The dressing is water soluble and dissolves when exposed to a large volume of liquid, such as copious blood flow. If the dressing dissolves, it may fail to form a good seal over the wound and clot formation becomes problematic. The inability of wound exudates to penetrate the dressing is another common disadvantage to achieving hemostasis in these prior art examples.

A review article by Lawrence L. K. Leung, *ACP Medicine*, Hematology XII—Hemostasis, 2003, discusses an alternative blood clotting mechanism: the initiation of an "intrinsic cascade" by a negatively charged surface like glass. The intrinsic cascade process, in this context, relates to the polymerization of fibrinogen into fibrin, a blood protein that lends structure to a blood clot. The use of silica powder as a procoagulant is mentioned in U.S. Patent Application Pub. No. 2006/0034935 A1 and in Stucky, Galen D. et. al., *Journal of the American Chemical Society*, 128:8384-8385, 2006, in which porous glass beads with calcium, a known co-factor in the clotting cascade, are recognized as a contact activator for the intrinsic clotting cascade. However, neither of these publications addresses the problem of supporting and maintaining the powder or glass bead silica in place after introducing it to a wound. Therefore, in wounds exhibiting high bleeding rates, the silica may be washed away instead of remaining at the injury site.

SUMMARY OF THE DISCLOSURE

A conformable structured therapeutic dressing has maximum available surface area of a therapeutic agent to stimulate therapeutic response in wounded tissue of a mammalian subject. In preferred embodiments, the therapeutic agent includes a procoagulant to arrest bleeding as quickly as possible to prevent life-threatening blood loss. The wound dressing exhibits a structured adsorbent that maximizes available surface area of a functional filler compared with that of the prior art. This is achieved by using a minimal amount of binder and small, porous particles of the functional filler. Minimizing the binder maximizes the amount of functional filler and reduces the chance that the binder will block access to the surface area of the functional filler. Small particles are desirable because they have a high surface area to volume ratio. Porous particles have a large amount of internal surface area. Structured adsorbents with higher surface areas, higher inter- and intra-fiber porosities, and low internal mass transfer resistances produce higher rates of mass transfer of an adsorbate onto the functional filler. High surface area structured adsorbents have greater adsorption capacity in a given volume and/or mass, because of the high ratio of functional filler to binder.

Several clotting mechanisms can contribute to hemostasis in a bleeding wound. In the context of bleeding wounds, the term blood encompasses blood components such as plasma, platelets, and various types of blood cells. In a preferred embodiment, stimulating and sustaining multiple clotting mechanisms simultaneously is achieved by incorporating multiple procoagulants—an intrinsic cascade initiator, platelet stimulator, and dehydrating agent—into one dressing. The prior art uses chitin derivatives like de-acetylated chitosan or salts of de-acetylated chitosan to stimulate platelet activation and platelet adhesion in blood clot formation. The prior art also mentions the use of silica powders and glass beads, but it does not teach a synergy achieved by combining silica, an intrinsic cascade initiator, with one or more other procoagulants, for example, chitosan and its derivatives (e.g., chitosan acetate or chitosan lactate).

A preferred embodiment of a bandage, also useful as a surgical sponge or battle wound patch, that includes multiple procoagulants cooperating in a synergistic fashion is, in general, formed of a fibrous, nonwoven article that is flexible and useful as a wound dressing for hemorrhage control. The nonwoven article is made of about 10 μm-50 μm sized macrofibers, comprising functional filler particles held together by a fine network of polymer microfibers ranging in size from about 5 nm-500 nm. The functional fillers are procoagulants or other therapeutic agents. Examples include, but are not limited to, zeolite, silica, chitosan, cationic chitosan salts, calcium, and mixtures of them. Procoagulant agents can be present as the sole therapeutic agent or present in combination with other therapeutic agents, such as an antimicrobial or anesthetic agent. The polymer fibers are ultrahigh molecular weight polyolefin or other polymers or mixtures of polymers.

This composite nonwoven article exhibits intra-fiber and inter-fiber porosity. Intra-fiber porosity means that there is free space around the functional filler particles within an individual fiber. Inter-fiber porosity means that there is free space between individual fibers. The resulting article has an unusually large amount of functional filler versus binder, and a correspondingly high surface area. Very little of the surface area of a functional filler particle is blinded by either the polymer binder or the other filler particles.

In one such preferred article, silica, a known intrinsic cascade initiator is the functional filler and is supported within a web of ultra-high molecular weight polyethylene (UHMW PE) microfibers. In preferred embodiments, a polymer composite, in which its polymeric web usually accounts for only approximately 5% by weight of the overall structure, and the functional filler, usually including a silica component, comprises the balance of approximately 95%, constitutes a "base fibrous article" (as it will be referred to hereafter). The inventors named on this patent application recognized that the base fibrous article composed of functional fillers such as silica and/or other blood clotting initiators has the advantage of wound conformability and high available surface area to rapidly contact wound exudates and rapidly initiate clotting.

In general, the base fibrous material can act as a substrate for many therapeutic agents. The term "therapeutic agent" is intended to include not only procoagulant and hemostatic agents, but other agents that might typically be applied to a wound to promote healing or other therapeutic response. One preferred hemostatic agent is chitosan or a chitin derivative having the characteristics described in U.S. Patent Application Pub. No. US2005/0137512. The chitosan products described in U.S. Patent Application Pub. No. US2005/0137512 are useful as the chitosan hemostatic agents used in the embodiments described.

Additional aspects and advantages will be apparent from the following detailed description of preferred embodiments, which proceeds with reference to the accompanying drawings.

BRIEF DESCRIPTION OF THE DRAWINGS

FIGS. 3A, 3B, 3C, 3D, and 3E are SEM images showing with increasing magnification an article of filled polymeric macrofibers composed of a functional filler of zeolite crystals incorporated into each of the macrofibers. The method of manufacture is similar to that used for the base fibrous article.

FIG. 7A shows an unlofted, uncoated article; FIG. 7B shows a lofted, uncoated article; and FIG. 7C shows a lofted article after it has been spray-coated with a chitosan lactate solution and then dried.

DETAILED DESCRIPTION OF PREFERRED EMBODIMENTS

Figure 1A:
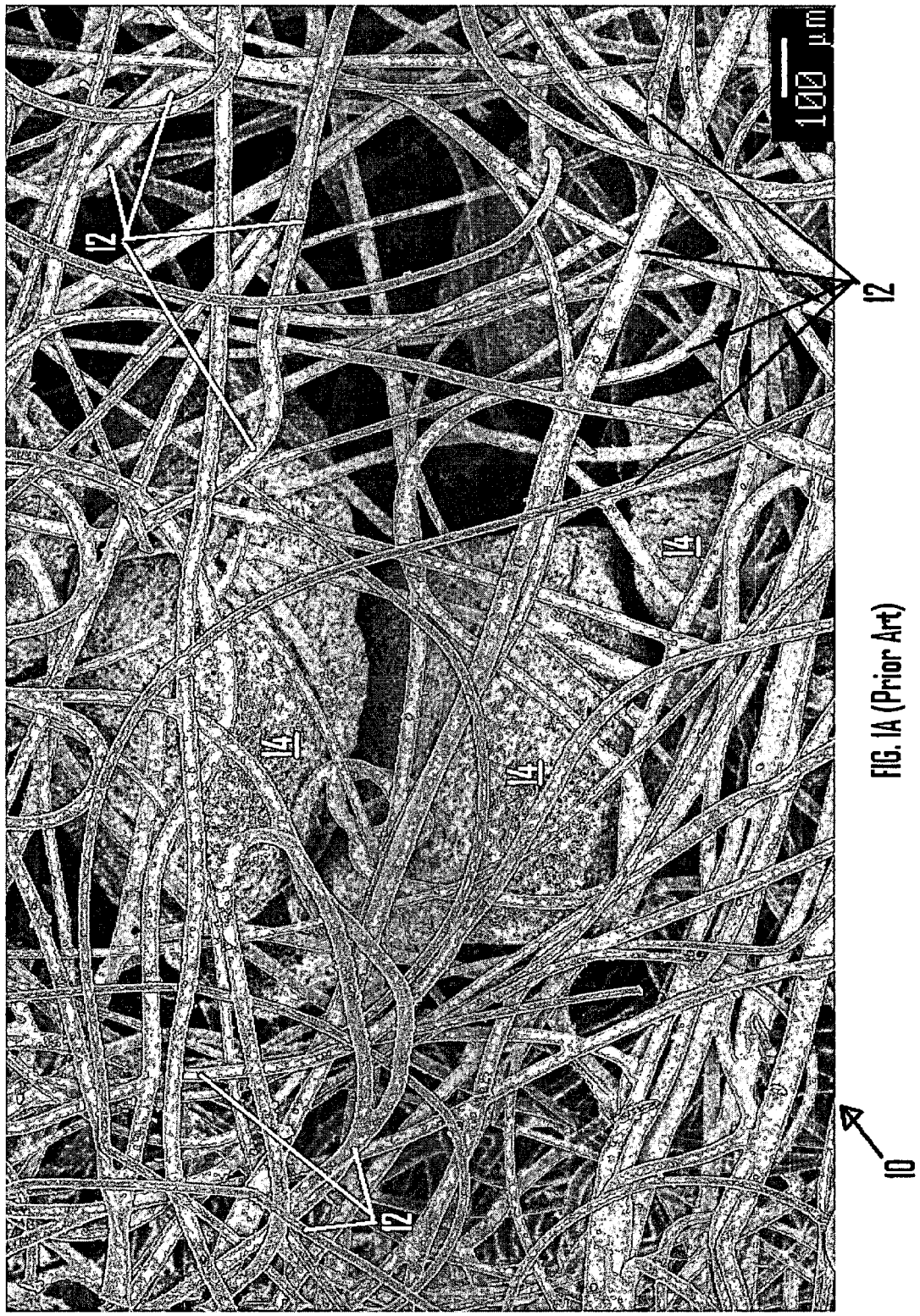
FIGS. 1A and 1B are SEM images showing structured activated carbon granules of a prior art AQF™ adsorptive filtration material and a prior art KX™ adsorptive filtration material, respectively.
Figure 1B:
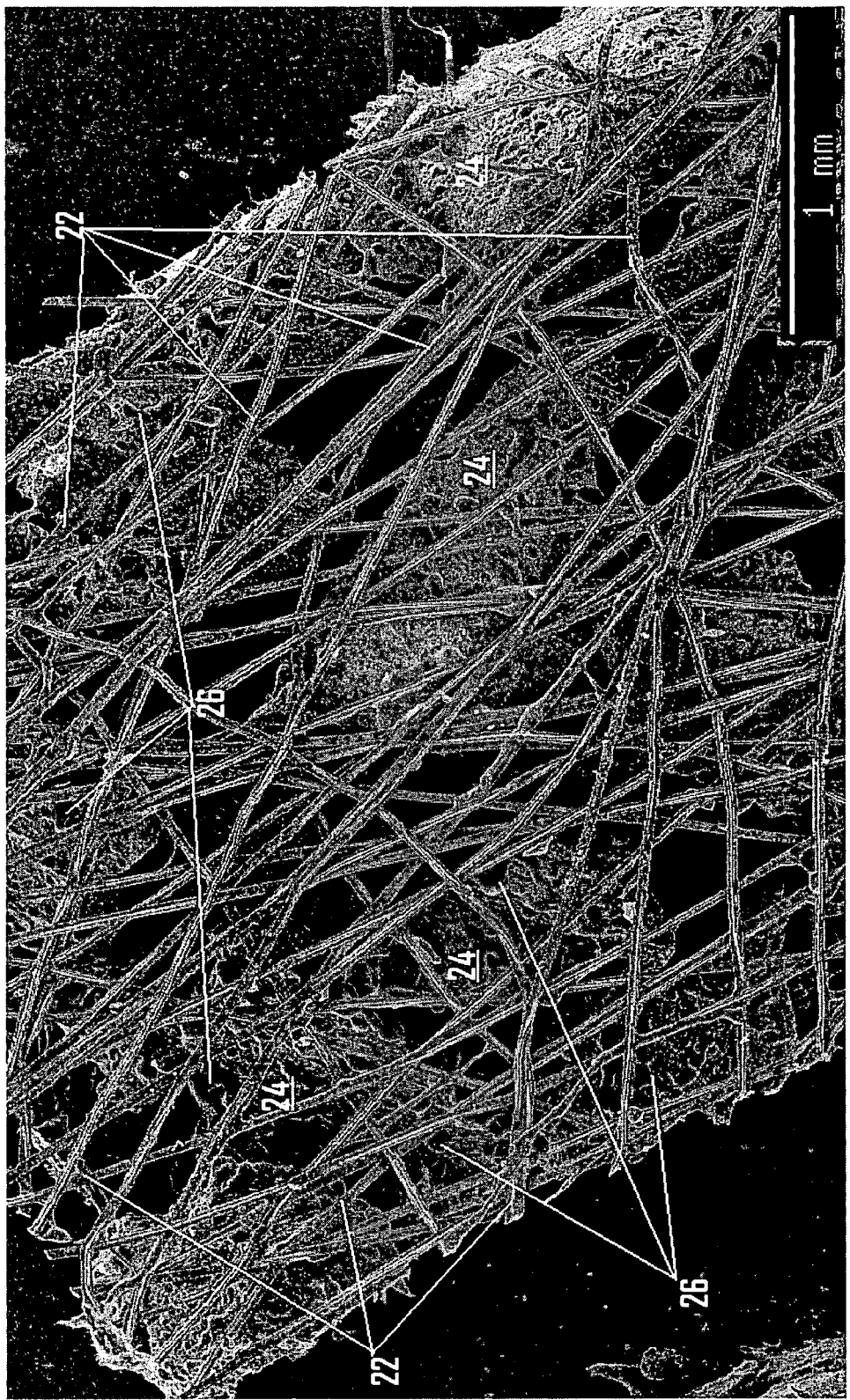
Figure 2:
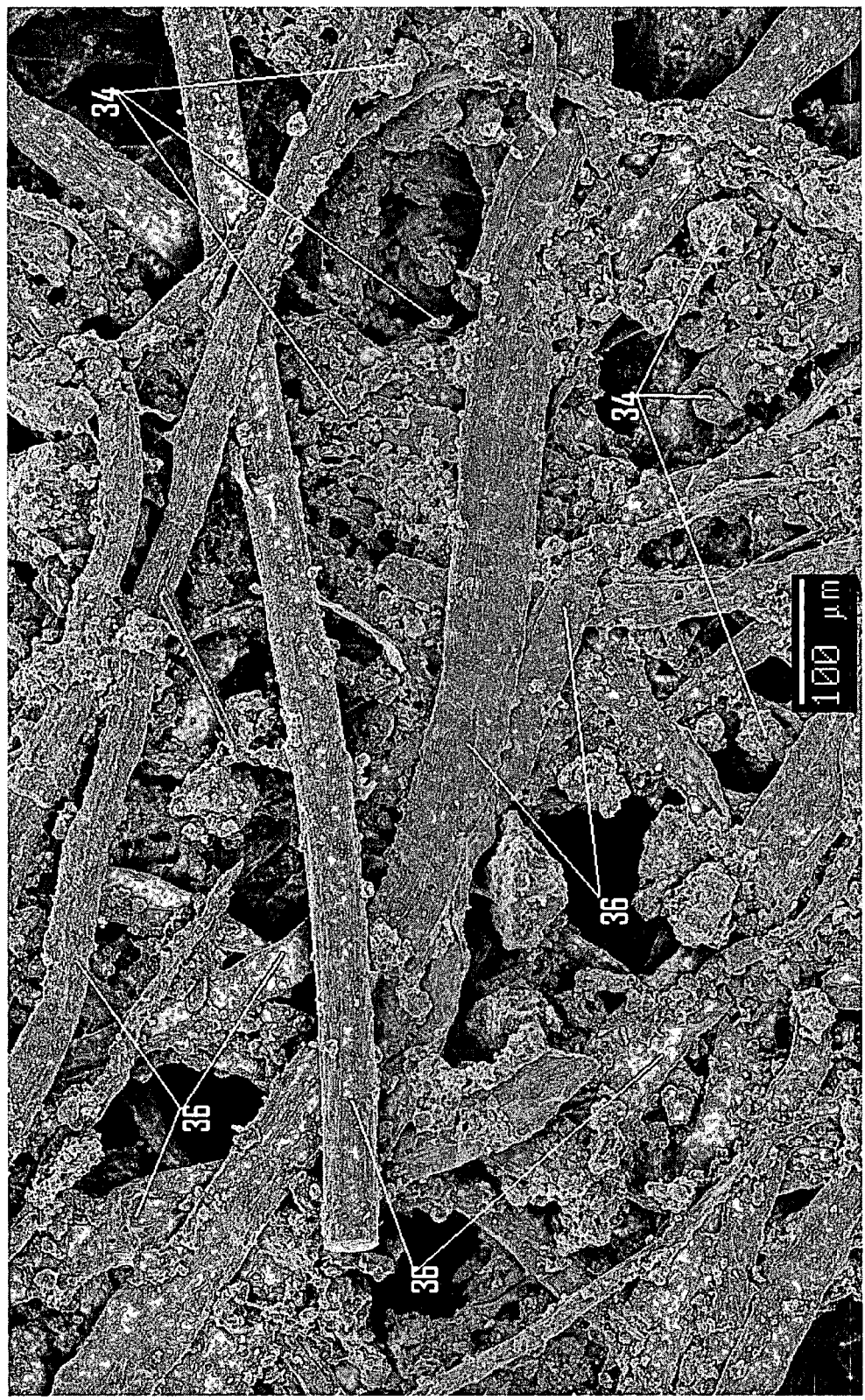
FIG. 2 is a SEM image showing activated granules adhered to the outside surfaces of a randomly configured fibrous substrate of prior art Lydall water filtration media.
Figure 3A:
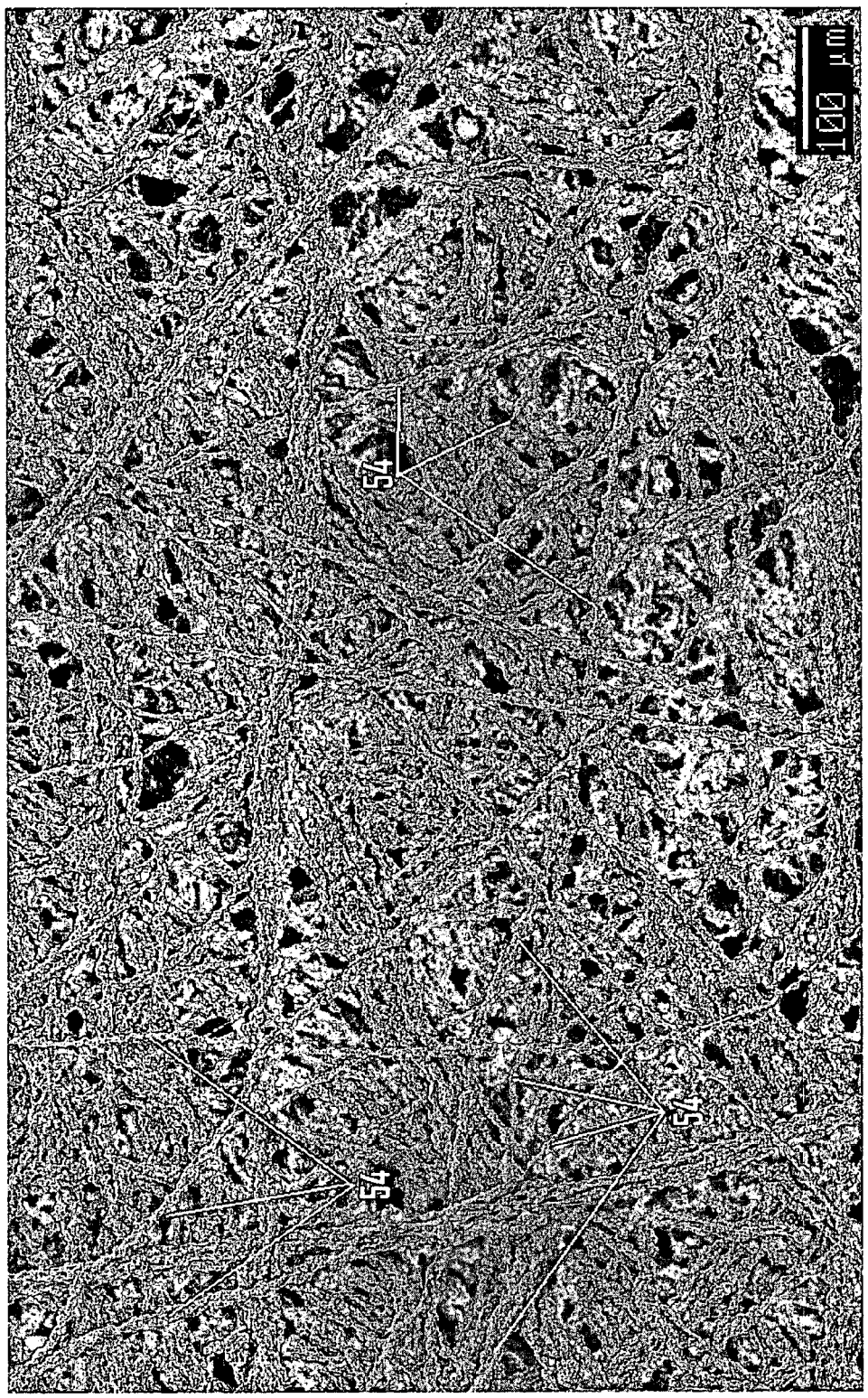
Figure 3B:
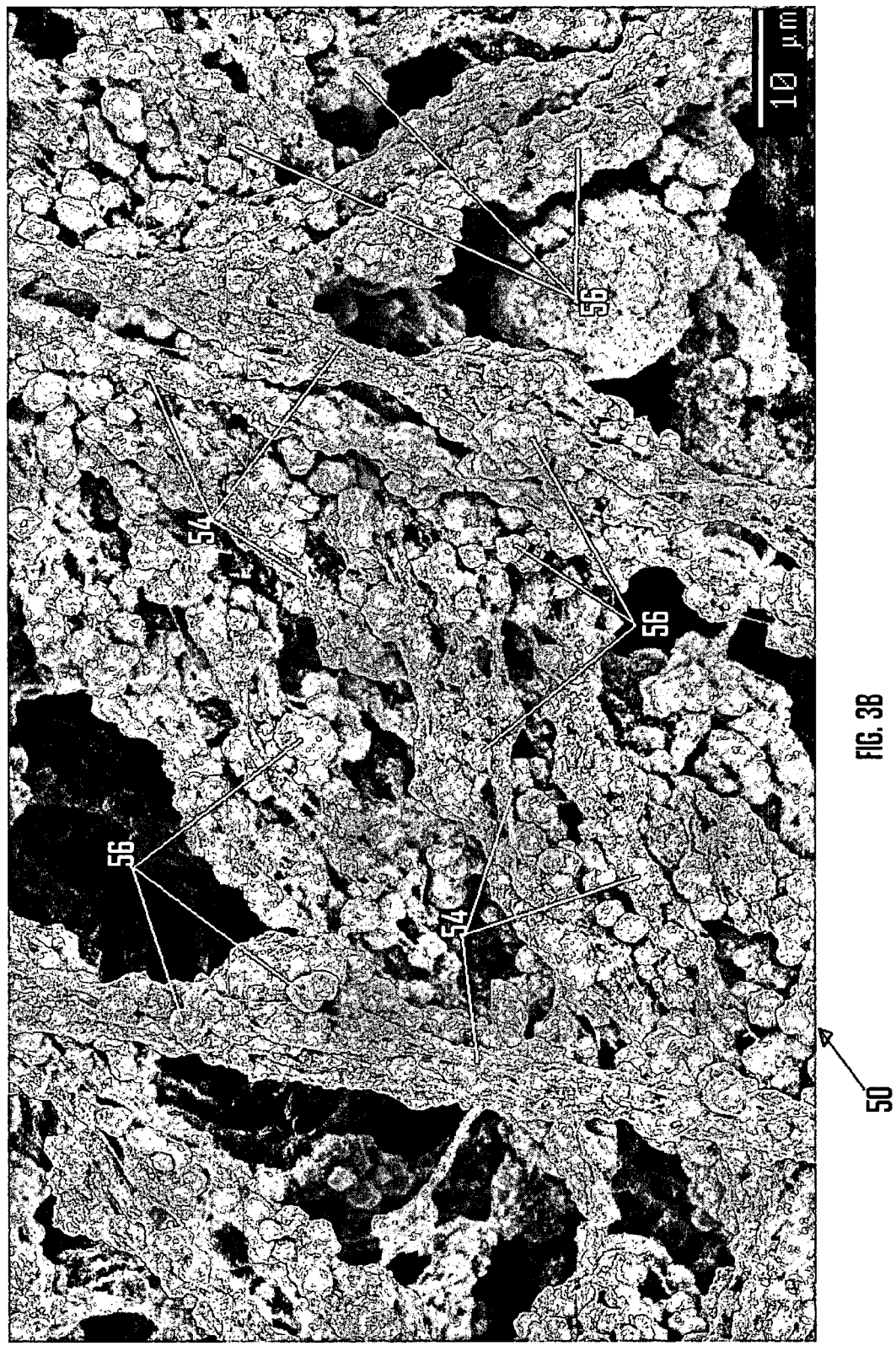
Figure 3C:
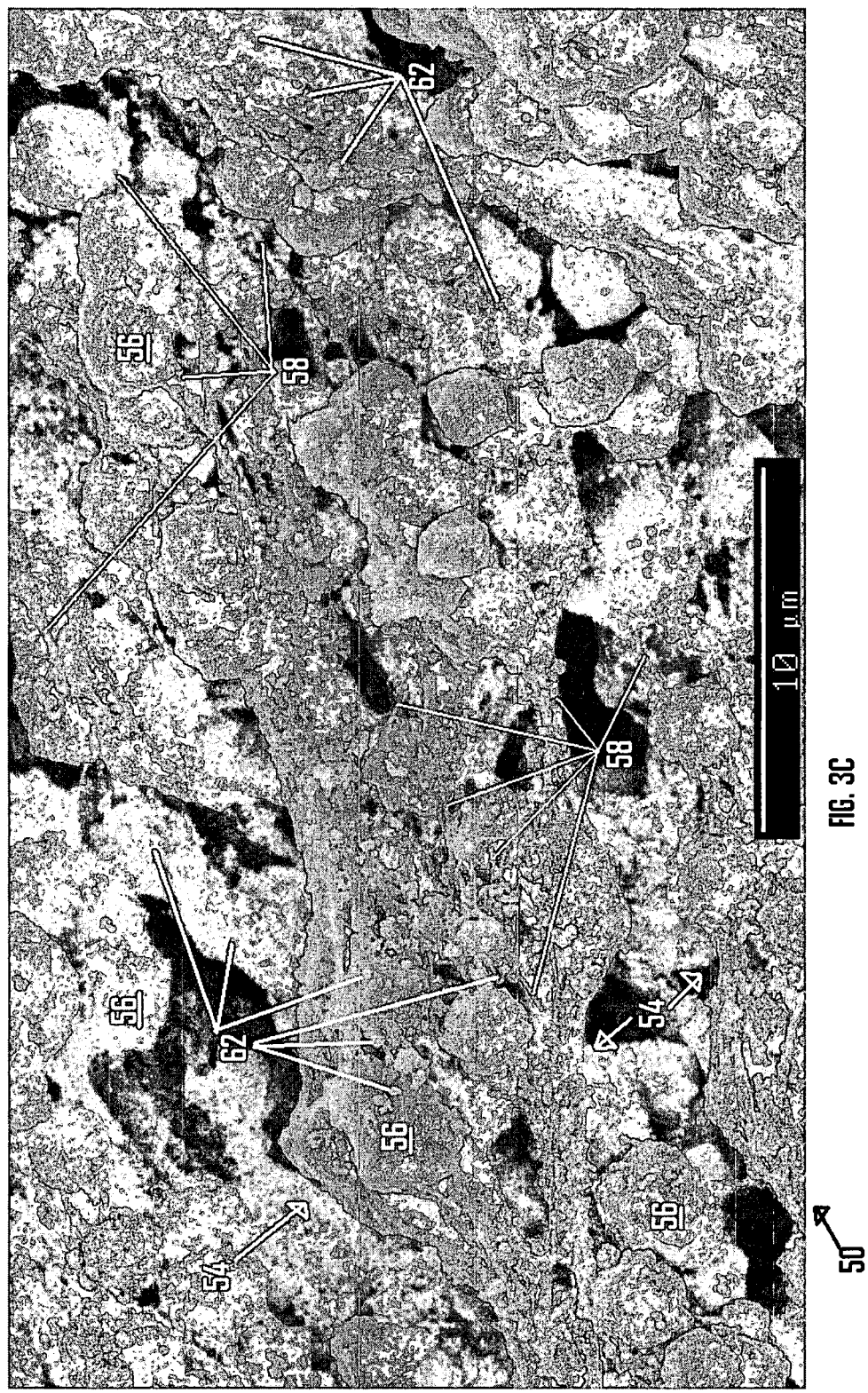
Figure 3E:
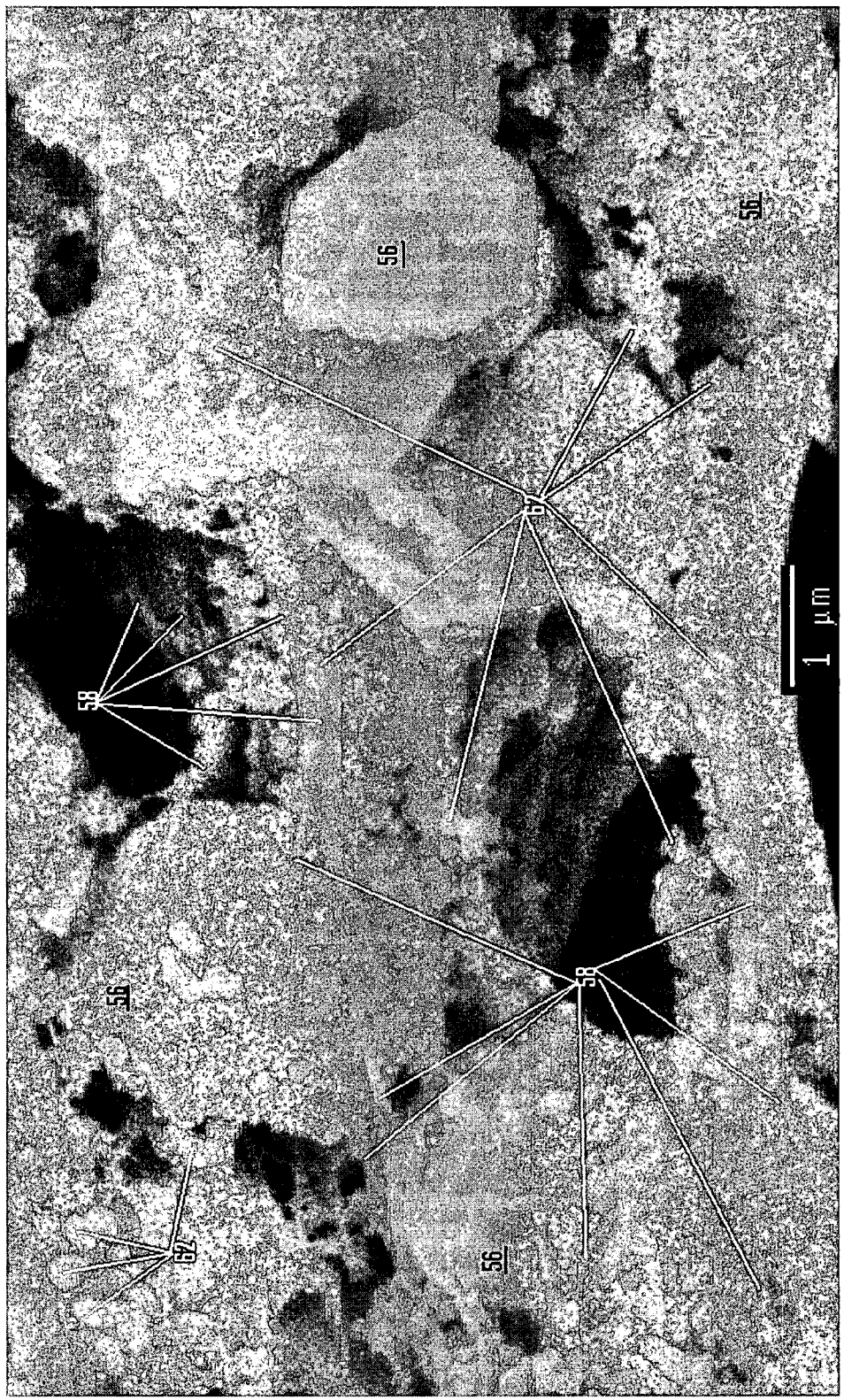

FIGS. 3A, 3B, 3C, 3D, and 3E show with increasing magnification an article 50 of filled polymeric macrofibers 54 composed predominantly of a functional filler of zeolite crystals 56 bound by microfibers 58 arranged in a network 60. FIG. 3A shows fibrous material 50 in the form of a nonwoven article. Network 60 of microfibers 58 functions as a binder and is made of ultrahigh molecular weight polyethylene (UHMW PE). The functional filler comprising zeolite crystals 56 is visible in FIGS. 3B, 3C, 3D, and 3E. Macrofibers 54 of a diameter size range from about 10 μm-50 μm are filled with about 80% by weight zeolite crystals of a particle size of about 3 μm supplied by UOP, LLC and 18% by weight Dupont Ti-Pure 105 titanium dioxide pigment, which functions as an inert filler. FIG. 3B shows in greater detail macrofibers 54 filled with discrete zeolite crystals 56. FIGS. 3C, 3D, and 3E show more clearly at higher magnifications that zeolite crystals 56 are held in place by network 60 of polymer microfibers 58. Polymer microfiber network 60 and filler particles form macrofibers 54. Polymer microfibers 58 are of a diameter size range from about 50 nm-500 nm. FIGS. 3C, 3D, and 3E also reveal observable intra-fiber porosity between adjacent zeolite crystals 56 and inter-fiber porosity between adjacent macrofibers 54. The zeolite crystals 56 are porous, and the fibrous structure does not blind this porosity. Since fluids can readily penetrate the inter-fiber spaces and intra-fiber pores to contact the high surface area filler, there can be very high rates of mass transfer between the fluid and fibrous article 50.

The example shown in FIGS. 3A, 3B, 3C, 3D, and 3E is a non-woven fibrous article. Different methods of manufacture could be used to produce, for example, a woven fabric, bulked continuous yarn, a membrane, or a film. However, fibrous article 50 is advantageous because its microfiber network 60 maintains flexibility of the material with a very high amount of functional filler. Suitability for different applications can be addressed by changing the functional filler, incorporating multiple functional fillers, or changing the material structure. Many different types of functional fillers can be used.

Figure 4A:
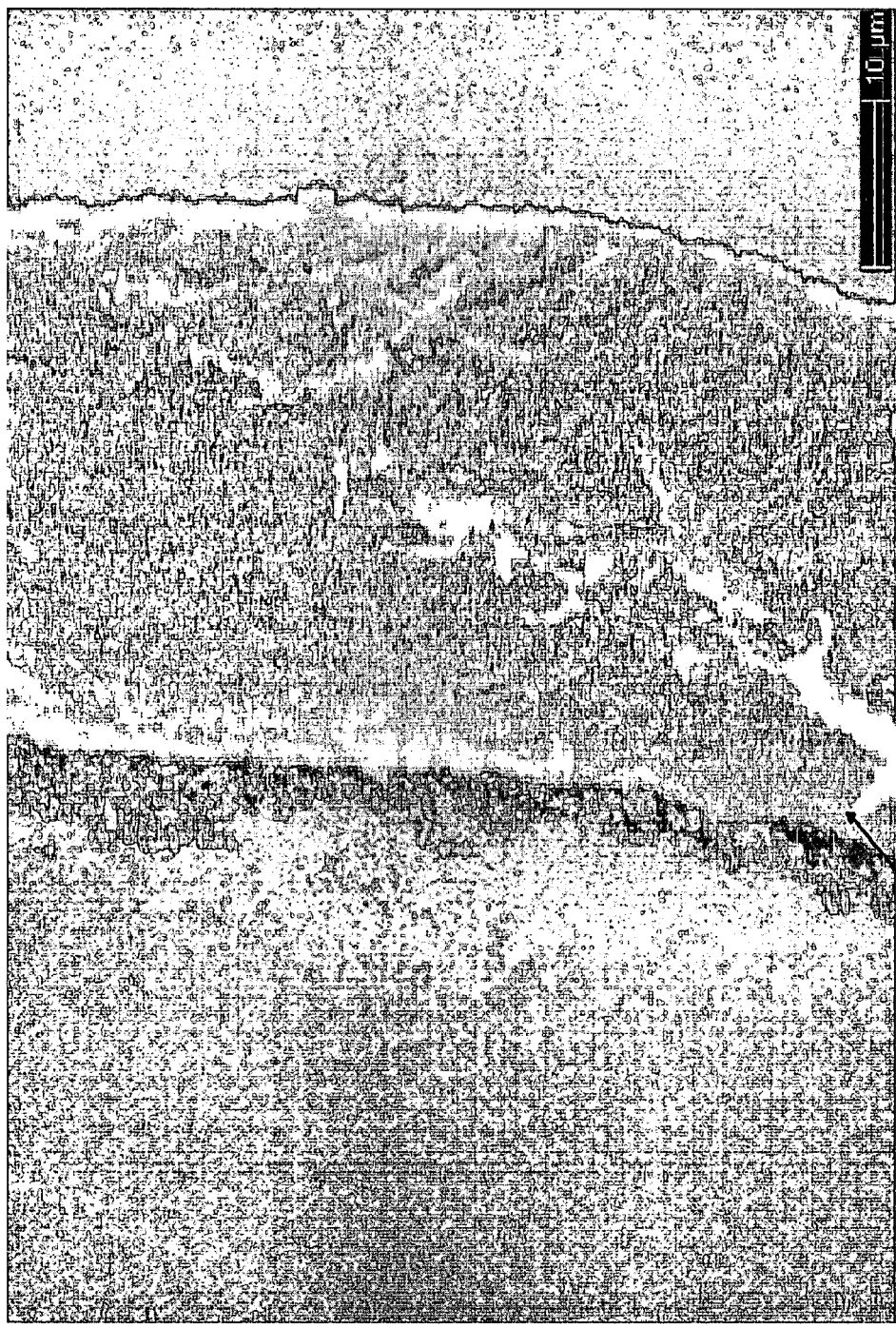
FIGS. 4A, 4B, 4C, and 4D are SEM images showing with increasing magnification of a polymeric macrofiber filled with fumed silica.
Figure 4B:
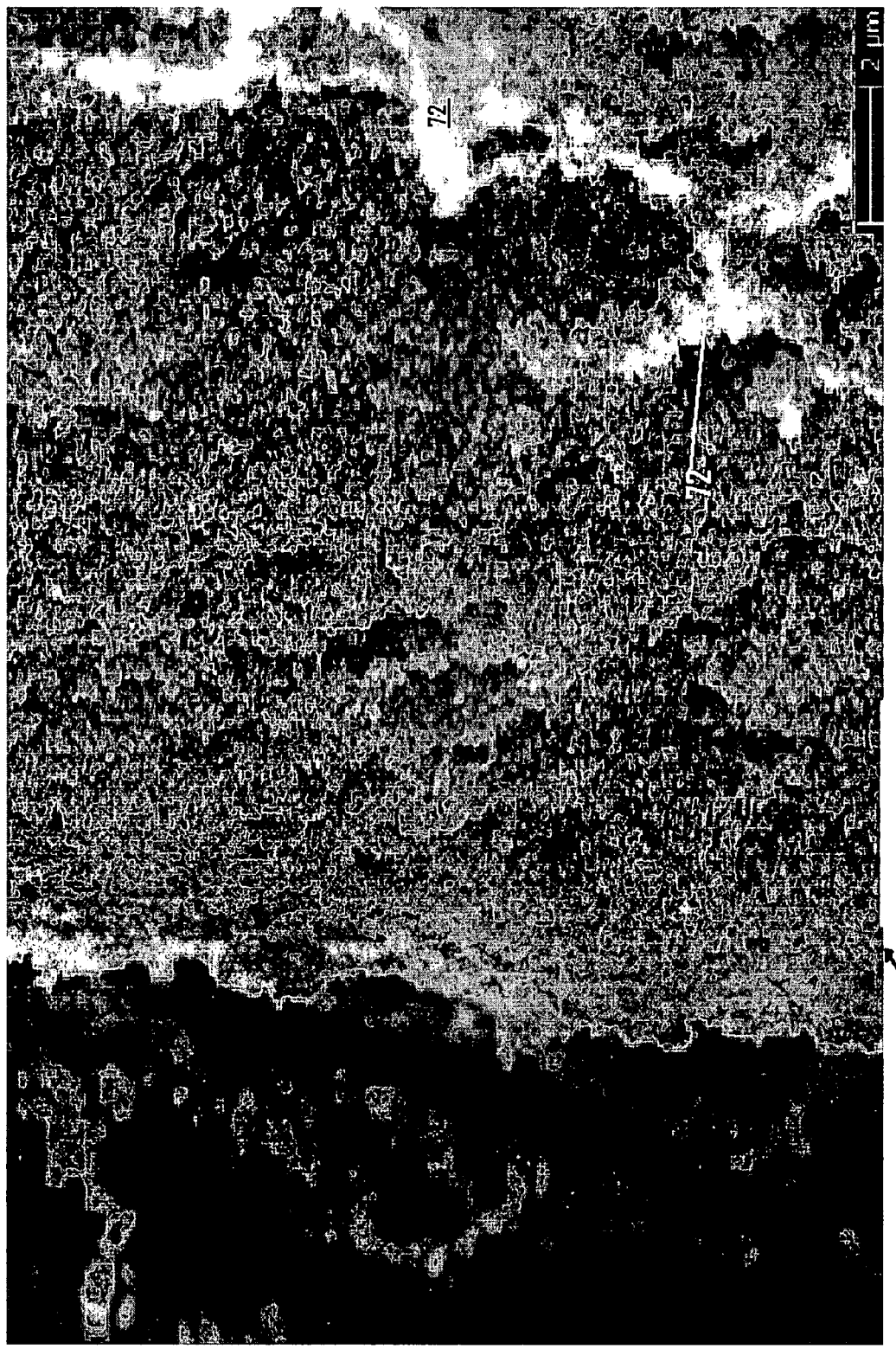
Figure 4C:
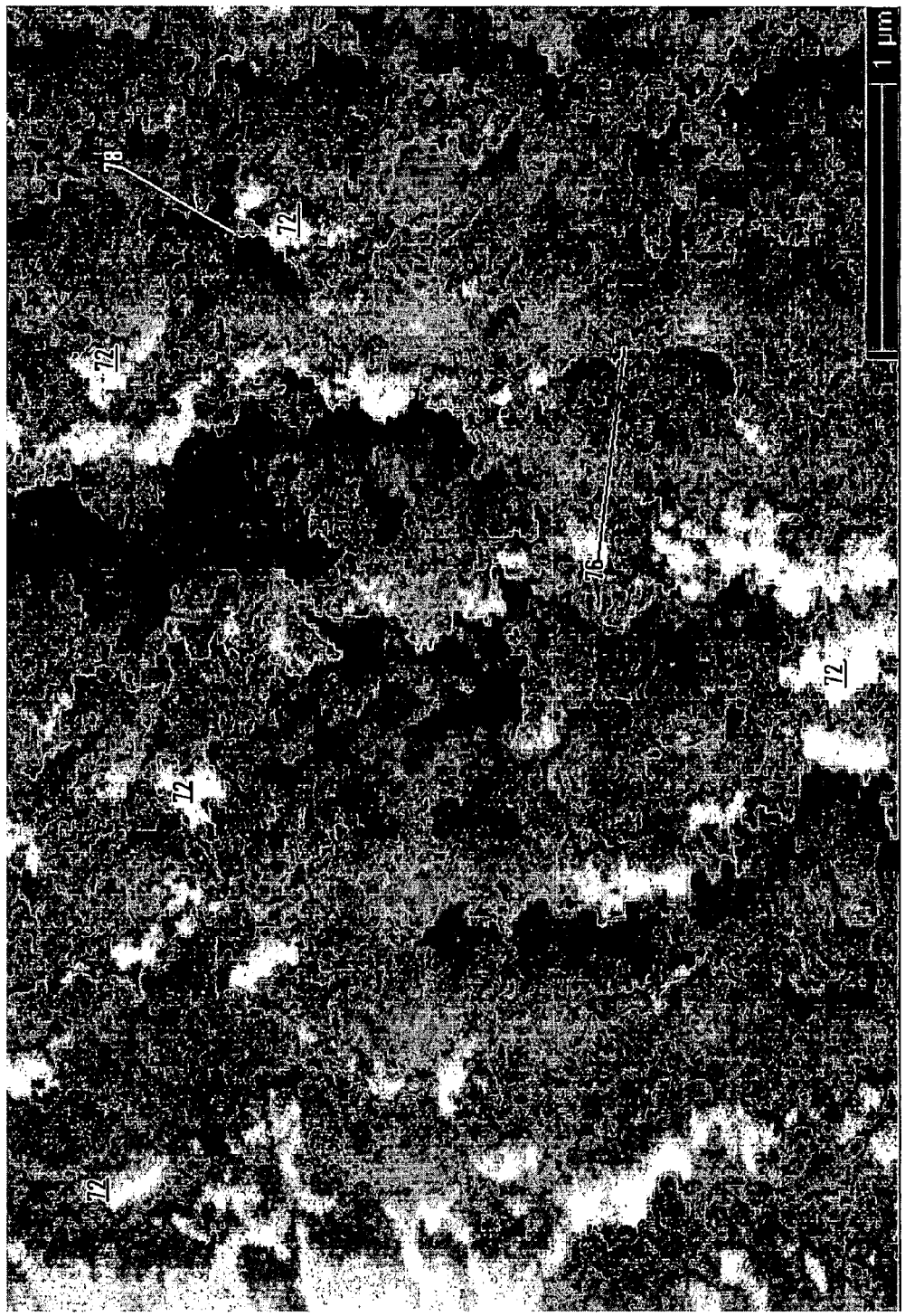
Figure 4D:
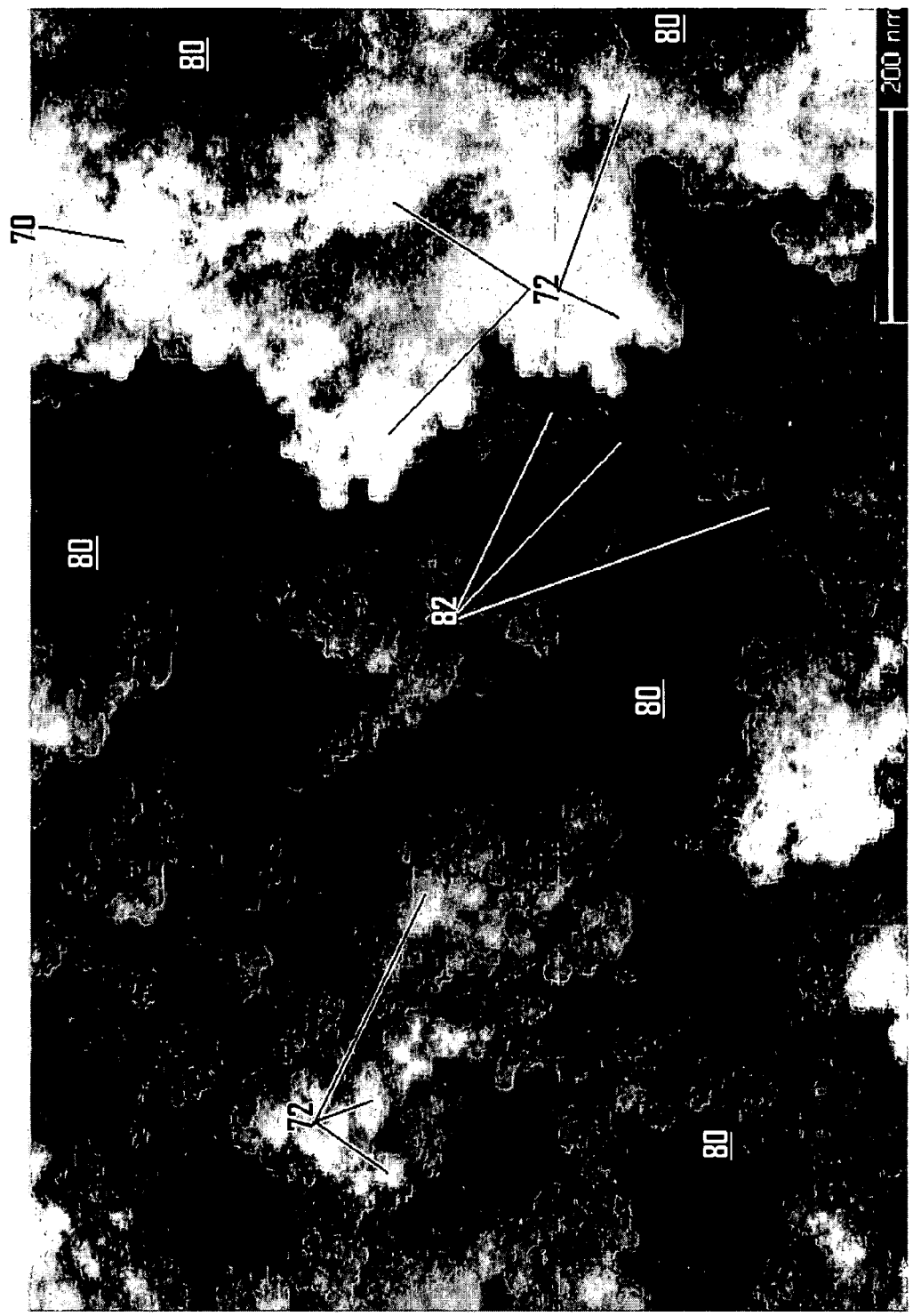

FIGS. 4A, 4B, 4C, and 4D show with increasing magnification an article of polymeric macrofiber filled with fumed silica. More specifically, FIG. 4A shows a macrofiber 70 of a fibrous article comprised of approximately 95% Cab-o-sil M5 fumed silica and approximately 5% Ticona 4120 UHMW PE, which hereafter is referred to as "fibrous article type A." FIG. 4B shows in greater detail macrofiber 70 of a diameter range from about 10 μm-30 μm filled with silica agglomerates 72 of fumed silica particles. FIG. 4C shows silica agglomerates 72 and UHMW polyethylene binder macrofiber 70 exhibiting intra-fiber porosity, where the dark regions are the pores. Reference numerals 76 and 78 point to the generally longitudinally oriented regions of binder that possibly includes some silica. Voids 80 between silica agglomerates 72, as shown on FIG. 4D, are intra-fiber pores that contribute to the intra-fiber porosity of macrofiber 70. Polyethylene fibers within the porous network are mostly obscured by silica agglomerates 72 but can also be seen with similar orientation. FIG. 4D shows microfibers 82 of polyethylene functioning as a binder.

Figure 5:
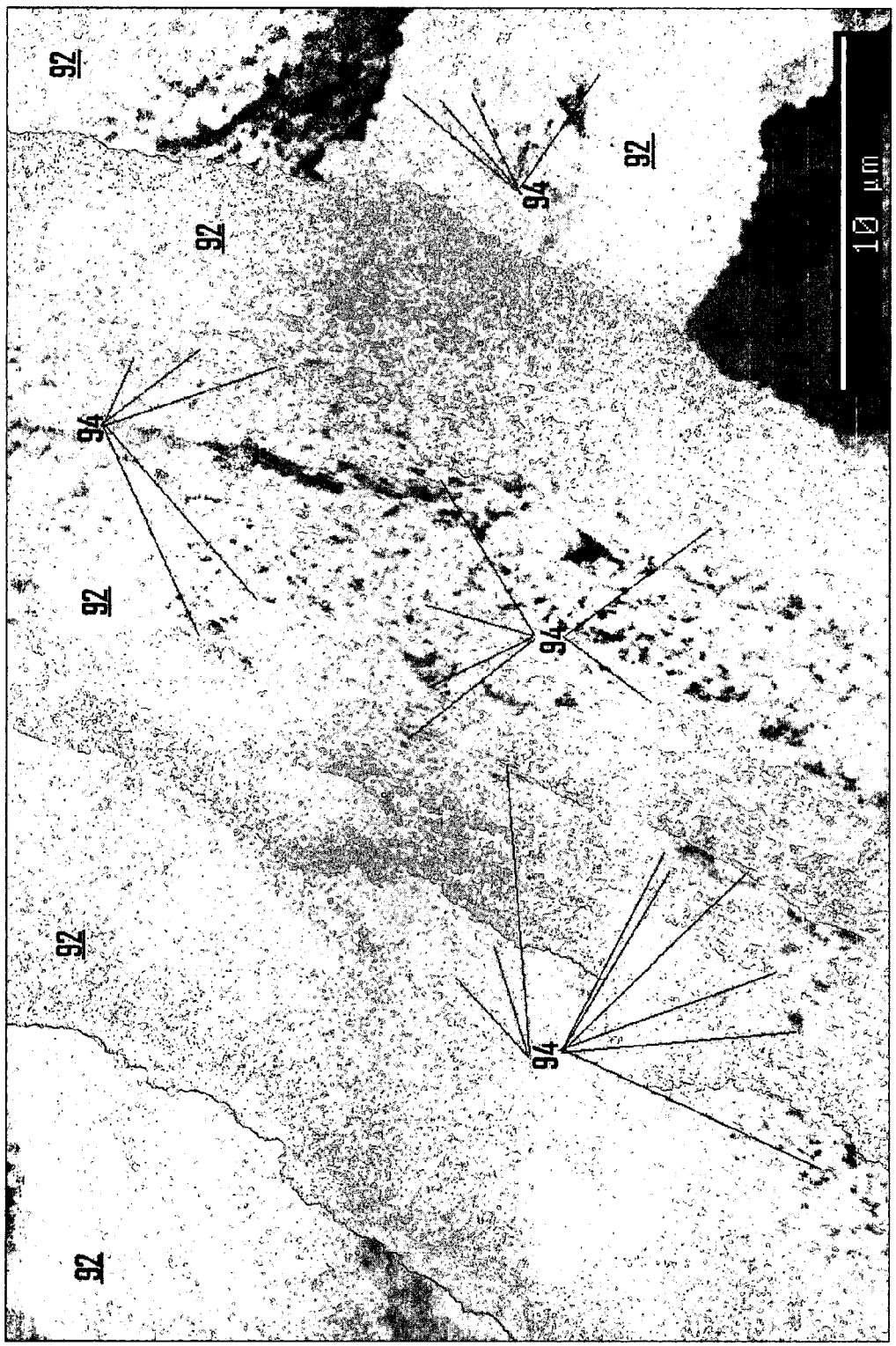
FIG. 5 is a SEM image showing an article of filled polymeric macrofibers composed of a functional filler of precipitated silica particles incorporated into each of the macrofibers.
Figure 6A:
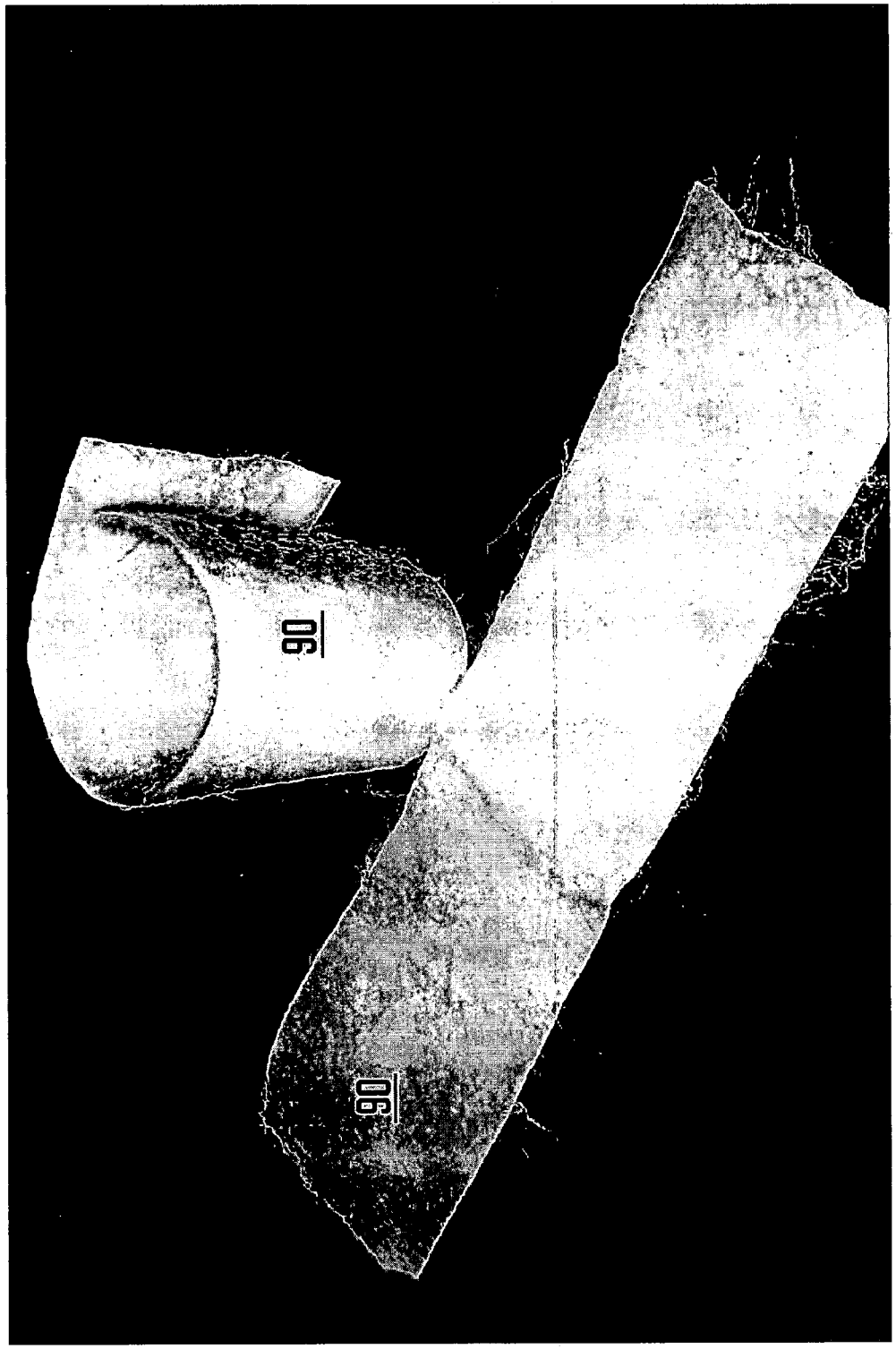
FIGS. 6A and 6B show different views of a nonwoven article of filled polymeric macrofibers.
Figure 6B:
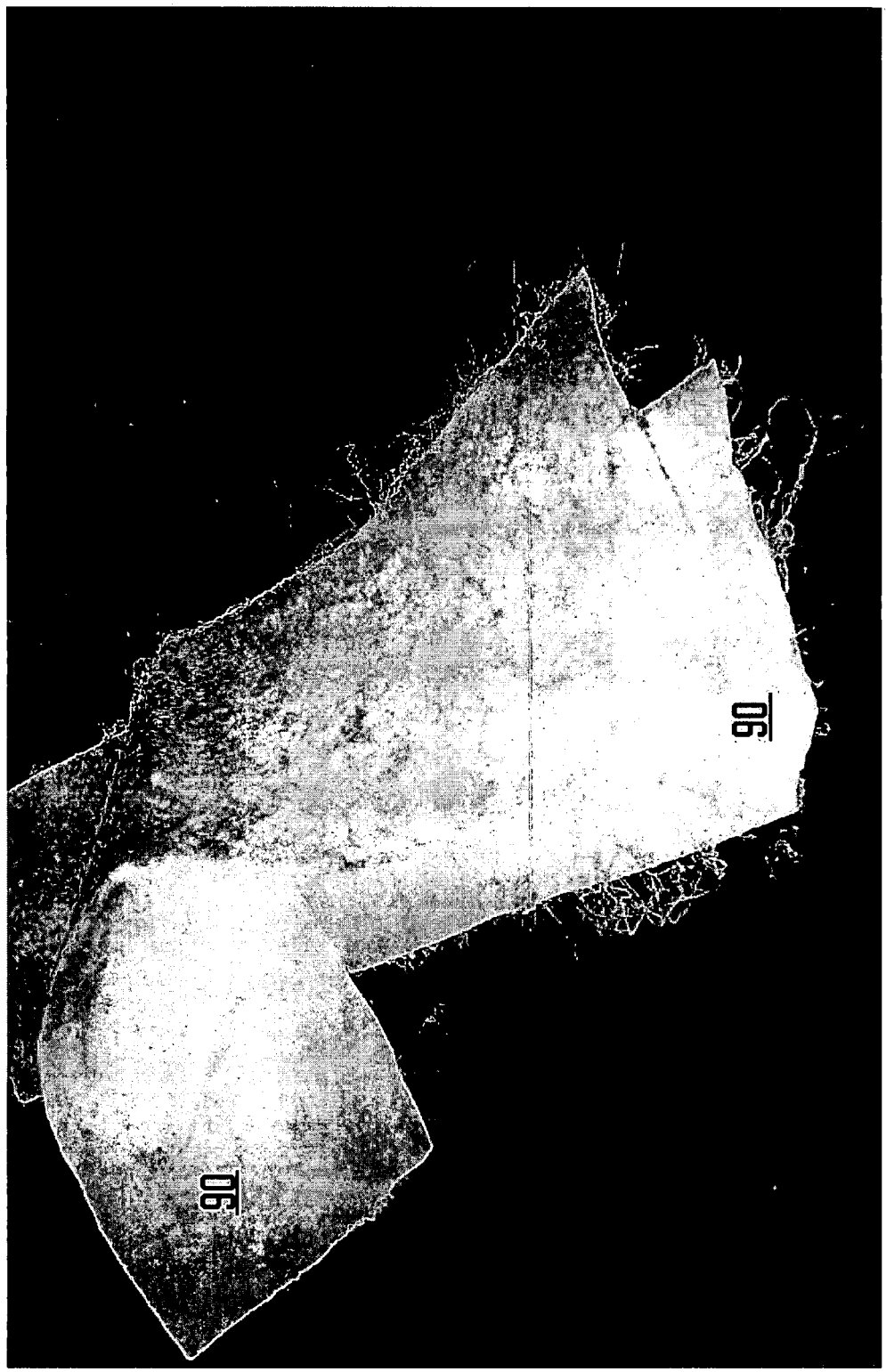

FIG. 5 shows another example of a fibrous article 90 in which precipitated silica is incorporated as a functional filler at a weight percent of about 94% and the fibers are UHMW PE. Inter-fiber spaces are exhibited among macrofibers 92 that are approximately 10 μm in diameter. Additionally, a network of microfibers 94 within macrofibers 92 exhibits intra-fiber porosity. A microfiber 94 measures about 100 nm in diameter. FIGS. 6A and 6B present images from different vantage points of representative sheet samples in a nonwoven fibrous article 90.

Each of the above examples demonstrates that the disclosed embodiments can apply to a wide range of functional fillers, all supported to allow for good distribution of the functional filler in a high surface area configuration.

Each preferred article of filled polymeric macrofibers is in the form of a wound dressing in a nonwoven configuration. The base fibrous article is fabricated by a process that entails forming a solid mixture of a polymer, such as an ultrahigh molecular weight polyolefin ("UHMW polyolefin"), a functional filler, a processing oil or plasticizer, and other minor ingredients. In preferred embodiments constructed with the base fibrous article, the functional filler may be comprised of a procoagulant agent in powder form alone or in combination with another therapeutic material or materials that may be in powder form. The mixture is fed to a plasticating device, such as an extruder, preferably a twin screw extruder, and mixed with additional processing oil to form a gel. The extruder disperses filler evenly throughout the fully developed gel, and then the gel extrudate is passed through a heated melt blowing die or melt spinning die. Under pressure, the die forces the gel through spinneret orifices to form individual macrofibers, which are then attenuated and cooled with pressurized air. During the cooling process, the gel solidifies, and the porous architecture within each macrofiber is formed. The processing oil drops out of the gel phase and fills the pores within the macrofibers. Oil-laden fibers of the extruded material are collected on a moving belt collector placed 30 cm-60 cm from the die, allowing them to randomly accumulate into a web, which is then peeled off the belt onto a wind-up roll. (Alternatively, to lessen the potential for degradation, one or more functional filler therapeutic materials can be added downstream of the polymer and oil feed ports in such cases in which one or both of the heat and shear of the extruder might cause degradation of the therapeutic material.)

All or most of the processing oil is subsequently extracted from the oil-laden fibrous web by exposing the rolls to a solvent. When the extraction process is complete, pores within and spaces between the macrofibers, formerly occupied by oil, are filled with solvent. The rolls are then dried in a 220° F. convection oven to drive off the solvent. A dried nonwoven article 100 is shown at 7.5× magnification in FIG. 7A. Article 100 is comprised of approximately 49% Cab-o-sil M5 fumed silica, 45% Hi-Sil SBG precipitated silica, and 6% Ticona 4120 UHMW PE, which is hereafter referred to as "fibrous article type B." Surface 102 of article 100 at this point is of three-dimensional character with macrofibers 104 standing out from surface 102. The material is denser than conventional gauze fabric.

Figure 7A:
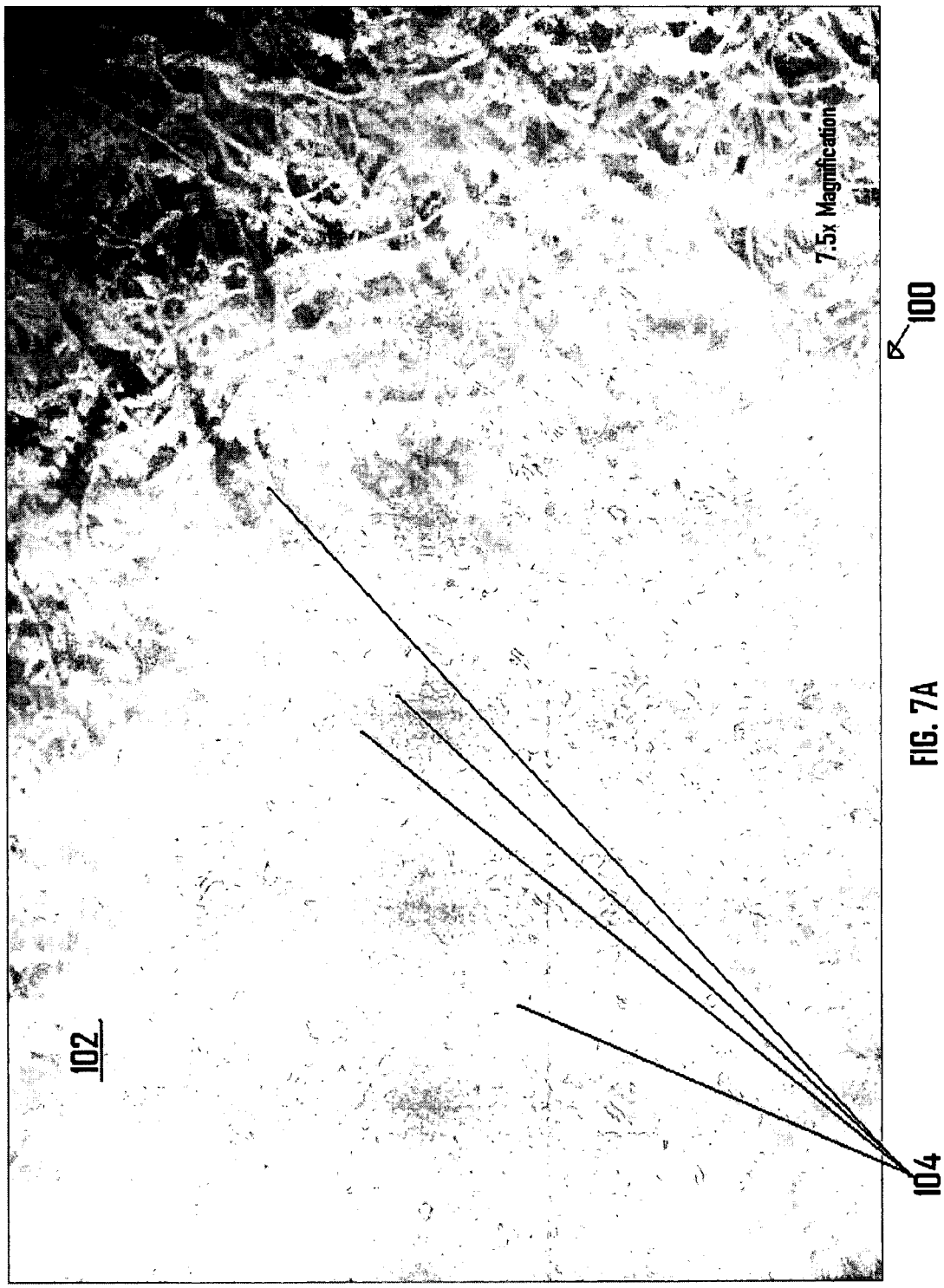
FIGS. 7A, 7B, and 7C are photographs showing at 7.5× magnification fibrous articles at various points in the manufacturing process.
Figure 7B:
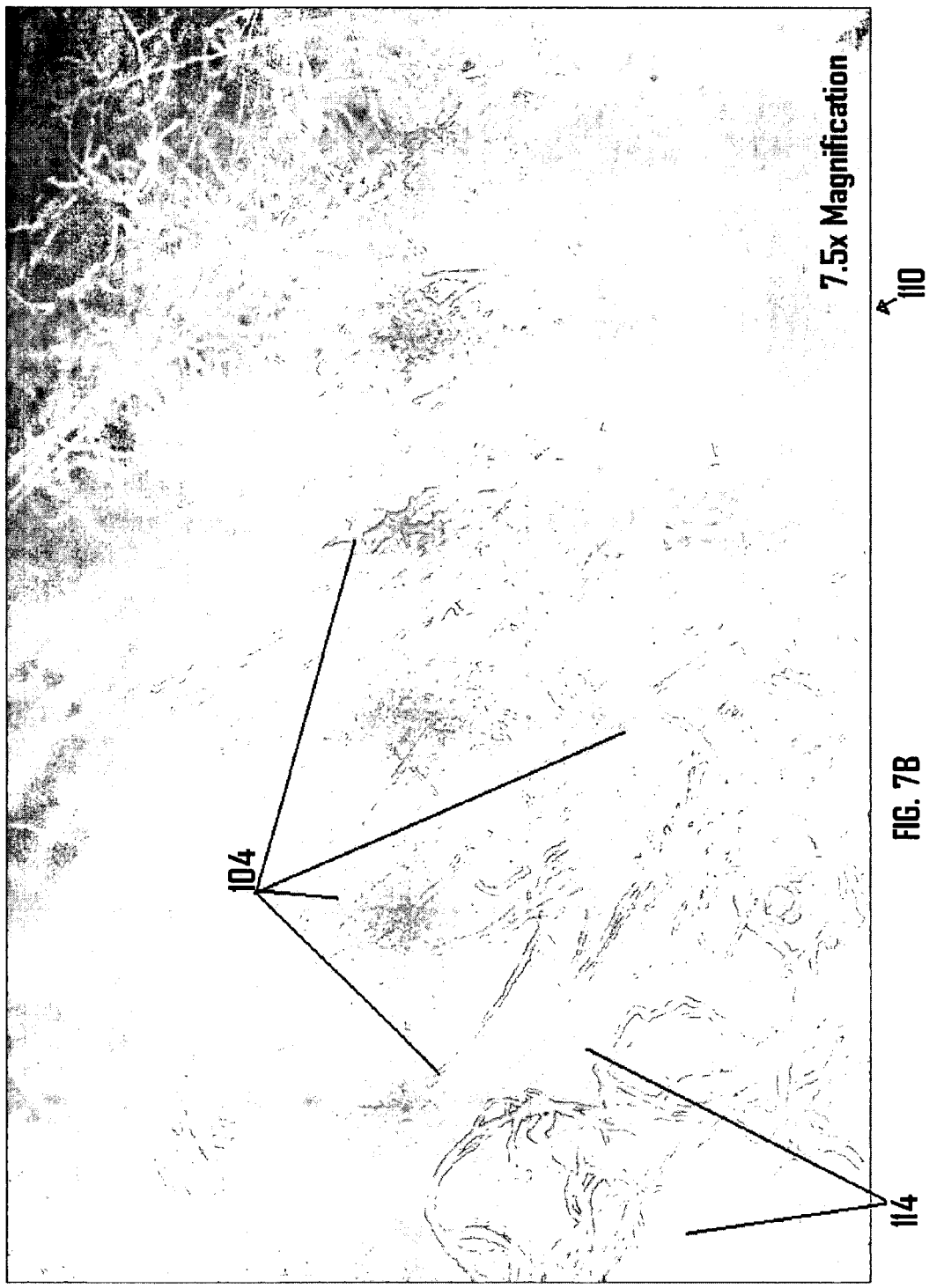

To loosen the tight structure of and expand inter-fiber spaces within article 100, 10 cm square samples of article 100 of FIG. 7A were air textured or lofted by manually applying in a circular motion a 60 psig jet of dry argon or nitrogen, thereby increasing its thickness by 100% or more. FIG. 7B shows, with the same magnification as that of article 100 of FIG. 7A, an article 110 that is a lofted version of article 100. Comparison of unlofted article 100 and lofted article 110 reveals that the longest of macrofibers 104 of lofted article 110 remain intact, but its inter-fiber spaces 114 are considerably larger.

Article 110 can be suffused with a therapeutic agent such as, for example, de-acetylated chitosan dissolved in a 1%-2% solution of lactic acid, with or without a blood clotting adjuvant such as a calcium compound additive. The suffusing therapeutic agent, in the form of a coating, is applied such that the therapeutic agent comprises between about 1% and 10% by weight of the finished article. The expanded volume achieved by lofting affords more opportunity for the chitosan coating to penetrate the material, accessing more surface area and adhering to more fibers. If the functional filler is negatively charged and the therapeutic agent is positively charged, adhesion of the coating may be aided by electrostatic attraction.

Figure 7C:
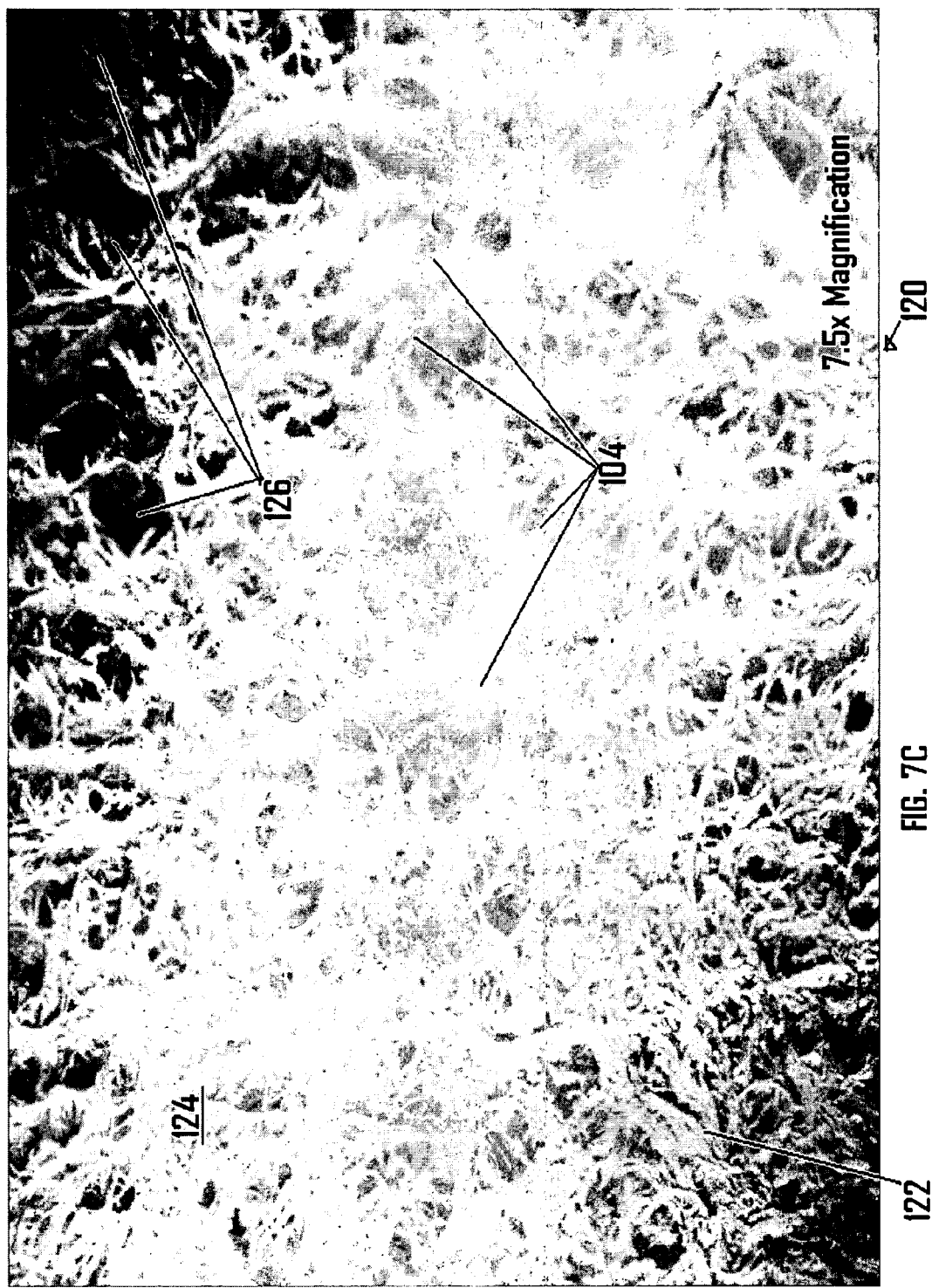
Figure 8:
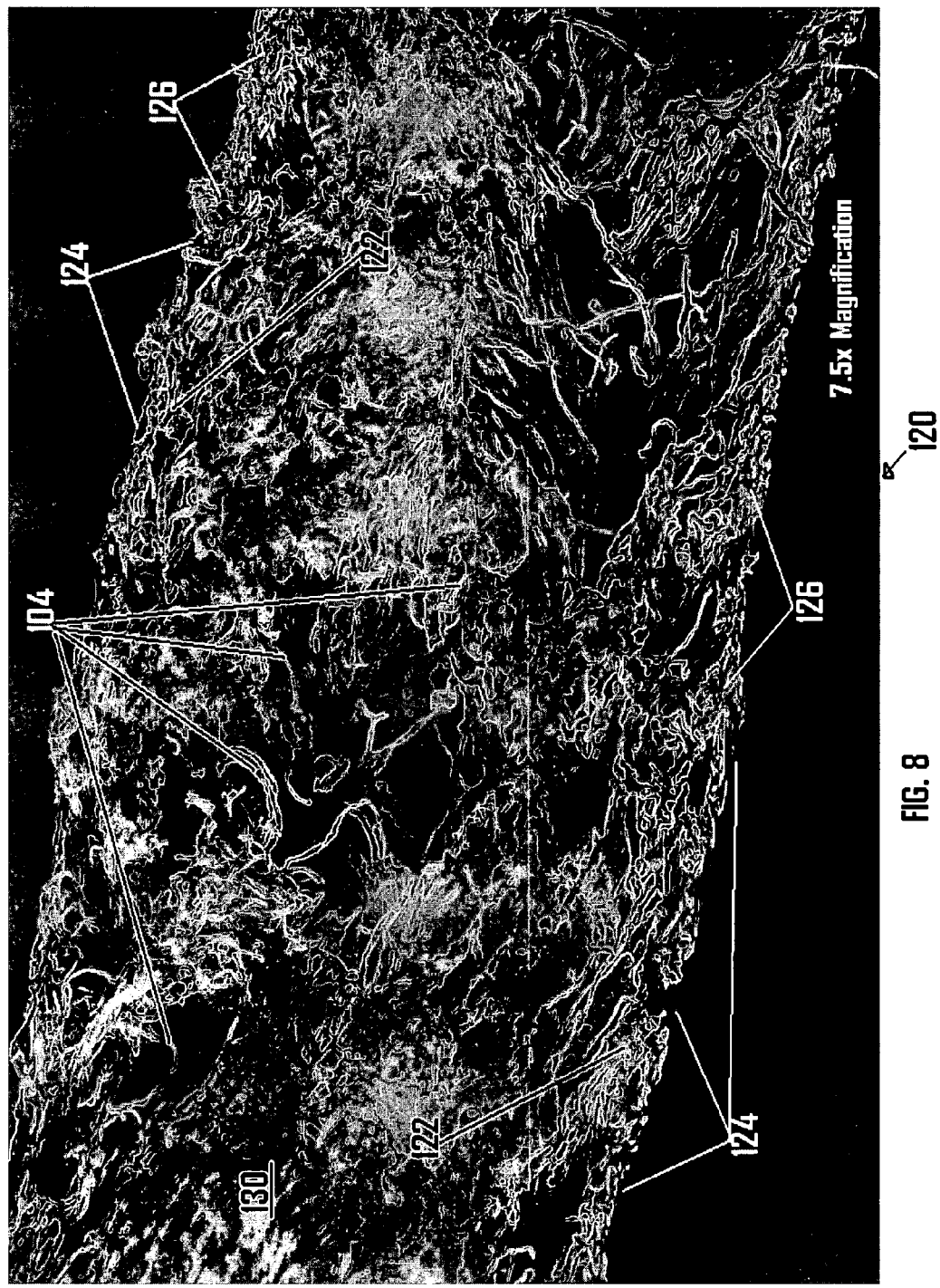
FIG. 8 is a photograph showing at 7.5× magnification a cross-section of a lofted, coated fibrous article of FIG. 7C, exhibiting by generally increasing amounts of lightness a progressively diminishing concentration of chitosan lactate coating from the surface (darker region) to the center (light region) of the article.
Figure 9:
FIG. 9 is a photograph showing at 10× magnification fibrous strands produced by hand shredding of the fibrous article of FIG. 8.

FIG. 7C shows an article 120 that is a chitosan-coated version of article 110 of FIG. 7B. Comparison of uncoated, lofted article 110 and coated, lofted article 120 reveals that a chitosan coating 122 of a surface 124 of article 120 compresses and fills in its inter-fiber spaces 126. FIG. 8, which is a cross-sectional view of coated, lofted article 120, shows that coating 122 covers macrofibers 104 at surface 124 and exhibits a more two-dimensional character that of surface 102 of article 100 and a preserved loft 130 in the interior of article 120. FIG. 9 shows that any one of articles 100, 110, and 120 can be shredded into strands 132, which may be advantageous in certain applications. Furthermore, it will be apparent to those skilled in the art that other configurations such as weaves, knits, tows, flocks, or expanded membranes are also possible by adopting other post-extrusion operations.

The basic process of forming porous macrofibers with very high functional filler to binder ratios is described in U.S. Pat. No. 5,093,197. Preferably, the polymeric component of the porous macrofibers is an UHMW polyolefin that forms a network in which one or more therapeutic agents are uniformly distributed and firmly held thereby with substantial exposure of their particulate surfaces. The large amount of procoagulant agent and other therapeutic agents held within the porous macrofibers presents a large surface area of such therapeutic agents, thereby greatly increasing the contact area between such agents and fluids from a wound site. The nonwoven configuration allows easy penetration of fluids from the wound site, thereby allowing increased contact between the therapeutic agents and the fluids. Such therapeutic agents are present in sufficient amounts to provide a wound dressing that may be hydrophilic even if the polymer is hydrophobic.

Although use of a UHMW polyolefin, and particularly UHMW PE, is preferred as the polymer component, other polymers and polymer mixtures may be used, as described in U.S. Pat. No. 5,093,197. Other polyolefin components (and mixtures of them) include polypropylene, metallocene polypropylene, polyolefin co-polymers, ethylene propylene co-polymers, and metallocene polymers. Alternative polymer components (and mixtures of them) include condensation polymers, such as polyesters, polyethylene terephthalate, polyamides, and polyimides; vinyl polymers such as polyvinyl chloride, polystyrene, and co-polymers of polystyrene; and natural polymers, such as the polysaccharides, chitin, chitosan, and cellulosic polymers.

The plasticizer employed preferably is a solvent for the polymer and a liquid at room temperature, although flash vaporization and wet spinning methods could also be employed. For UHMW PE, the solvating temperature would be preferably in the range of between about 160° C. and about 220° C. It is preferred to use as the plasticizer a processing oil, such as a paraffinic oil, naphthenic oil, aromatic oil, or a mixture of two or more such oils. Examples of suitable processing oils include oils sold by Calumet Lubrication Company, such as Calpar 325; Shell Oil Company, such as ShellFlex™ 3681, Gravex™ 41, and Catenex™ 945; oils sold by Chevron, such as Chevron 500R; and oils sold by Lyondell, such as Tufflo™ 6056. Oils and derivatives of oils obtained from green plants, such as esterified soy bean oil, can also be used as the plasticizer. Examples of suitable plant-based oils and/or derivatives of plant-based oils include SOY CLEAR™ and SOY GOLD™ offered by AG Environmental Products.

Any solvent suitable for extracting the processing oil from the fibrous article may be used in the extraction process. The solvent may be a hydrocarbon, halogenated hydrocarbon, or a hydrofluoroether. Suitable hydrocarbon or halogenated hydrocarbon solvents include 1,1,2-trichloroethylene, perchloroethylene, 1,2-dichloroethane, 1,1,1-trichloroethane, 1,1,2-trichloroethane, methylene chloride, chloroform, 1,1, 2-trichloro-1,2,2-trifluorethane, isopropyl alcohol, ethanol, methanol, diethyl ether, acetone, methyl ethyl ketone, hexane, heptane, and toluene. Suitable hydrofluoroethers include methyl or ethyl nonafluoroisobutyl ethers, or mixtures thereof, and methyl or ethyl nonafluorobutyl ethers, or mixtures thereof.

Minor ingredients, constituting less than about 20% by weight of the extracted web, may be employed. Such minor ingredients may include, for example, nontoxic antioxidants, lubricants, pigments, polymer modifiers, processing aids, and thermal stabilizers.

The therapeutic agent or agents preferably constitute from about 20% by weight up to about 98% by weight of the fibrous article and are firmly held in place within the article. Although typical filler levels are above 85% by weight and could reach 98% by weight, a much smaller fraction of the therapeutic agent that is appropriate to achieve a therapeutic response could be used in combination with an inert filler acting as a diluent of the therapeutic agent. The non-woven macrofibers that make up the article at micrometer length scales include therapeutic filler(s) contained within and bound by a network of sub-micron diameter polymer microfibers. The macrofibers have diameters that are generally in the range of 5 µm-500 µm. The result is that the particles of therapeutic agents are held firmly in place and in a high surface area configuration to allow for effective interaction with the wound and the fluids exuding from the wound site.

Procoagulant functional fillers include intrinsic cascade initiators, platelet stimulators, dehydrating agents, or mixtures of them. Specific procoagulant functional fillers include, but are not limited to, silica, zeolite, polysaccharides, starch, chitin and its derivatives, sorbent polymers, kaolin, celite, alum, thrombin, fibrinogen, fibrin, alginate, recombinant factor VIIa, diatomaceous earth, carbon, von Willebrand factor, fibronectin, vitronectin, thromboxane A2, thrombopoietin, intracellular adhesion molecule (ICAM)-1 and -2, vascular cell adhesion molecule (VCAM), aggretin, adenosine-di-phosphate (ADP), Ristocetin, and collagen. Other useful procoagulant agents are comprised of cationic chitosan salts, including, but not limited to, chitosan formate, chitosan acetate, chitosan lactate, chitosan maliate, chitosan chloride, chitosan ascorbate, and chitosan citrate.

Some zeolites and some silicas are known to staunch bleeding, and they may be used as the procoagulant agent either by themselves or in combination with one or more of chitosan, chitosan derivatives, and cationic chitosan salts. Whenever zeolites and/or silica and/or other procoagulant agents are used in admixture with chitosan and/or cationic chitosan salts, as functional fillers, the chitosan and/or cationic chitosan salts are preferably present in an amount so that the total filler level is less than about 98% by weight of the fibrous article. Therefore, the phrase "procoagulant agent" as used herein is intended to include a single procoagulant agent or a mixture of procoagulant agents. The procoagulant agent may be used in powder form, preferably having a particle size or particle size range that maximizes the procoagulant action of the procoagulant agent. The amount of procoagulant agent used is that which is effective in reducing blood loss from a wound as compared with that achievable with use of standard cotton gauze.

Other agents that might typically be incorporated into the fibrous wound dressing to promote healing include antimicrobial agents, i.e., any compound that stops, prevents, or destroys the growth of microorganisms. However, few conventional antimicrobial agents are capable of withstanding the high temperatures encountered in forming the fibrous dressing. It has been found that a suitable antimicrobial agent that can be incorporated into the dressings are silver nanoparticles, such as those described in U.S. Pat. No. 6,720,006. Silver nanoparticles have both antibacterial and antifungal properties. A useful particle size for such silver nanoparticles is in the range of 1 nm to about 50 nm, preferably from about 2 nm to about 10 nm, and most preferably between about 5 nm and about 8 nm. The amount to be incorporated into the fibrous dressing is an amount providing an effective antimicrobial activity, but less than a cytotoxic silver concentration. Skilled persons will appreciate that antimicrobial agents that are sensitive to temperature processing conditions during the formatting of the fibrous dressing could be applied as a post treatment. The advantage of silver nanoparticles is that they could be included before the macrofiber formation step or be applied as a post treatment.

Because of the advantageous properties of the base fibrous material, several embodiments fabricated with the base fibrous material were developed and tested in a series of in-vitro and in-vivo experiments documented below, totaling 14 trials. These trials are grouped according to the variation of base fibrous material used. The first version, referred to as "fibrous article type A" was used in Examples 24. As stated above, fibrous article type A includes approximately 95% Cab-o-sil M5 fumed silica and approximately 5% Ticona 4120 UHMW PE. Examples 24 tested fibrin formation in the blood clotting process, activated primarily by the silica component. As discussed in Example 5, fibrous article type A was then lofted using pressurized nitrogen to lower the bulk density and increase the inter-fiber separation. The more open structure of the lofted article can result in improved penetration of wound exudates.

Such a base fibrous article can be further enhanced by the addition of one or more procoagulants to activate multiple clotting mechanisms, for example, fibrin formation associated with the intrinsic cascade, platelet stimulation, and agglutination of red blood cells. The structure of the article may also contribute to the filtration and concentration of platelets and red blood cells. Additionally, it is known that silica has an affinity for enzymes and proteins that may contribute to the clotting process. Furthermore, dehydration of blood near the wound can also aid hemostasis by concentrating clotting factors. Silica is known to be hydroscopic, but sorbent polymers could also be used as a functional filler or coating to aid in dehydration. Finally, the fine microfiber network of the base fibrous article provides a scaffolding to which fibrin can attach. These multiple clotting mechanisms, working independently or cooperatively, result in an improved hemostatic article.

A method of preparing a chitosan solution that can be spray-coated onto the base fibrous article is described, for example, in the above-referenced U.S. Pat. No. 5,900,479. Being polycationic, chitosan adheres electrostatically to oppositely charged silica particles through ion pairing and, once dried, achieves a good coating on surface layers of the silica-filled fibrous article. The method of coating used for the articles described herein is spray-coating. Spray coating the fibrous article results in a heavier coating of chitosan or its derivatives on the surface layers of the product. The coating is therefore non-uniformly distributed throughout the article, with a higher concentration at the surface, decreasing to low concentrations at the center. Since the coating adheres more readily to the surface, a fibrous article that presents a large surface area is advantageous because it can carry more of the chitosan coating. The inventors postulate that the distribution of the coating and the presentation of the platelet stimulator followed by exposure to silica is synergistic and results in a faster and more robust clot. An extension of this art entails treating any fibrous web, for example cotton gauze, with a solution containing both a platelet stimulator and an intrinsic cascade initiator.

Fibrous article type A was spray-coated with chitosan lactate solution to investigate the effectiveness of combining two procoagulant agents: M5 fumed silica distributed homogeneously throughout the article, together with chitosan lactate. Examples 6-9, relating to in-vivo testing on internal mammalian wounds, demonstrate the effectiveness of this modification to the base fibrous article in arresting significant blood loss in a surgical situation. Once a bandage fashioned from coated fibrous article type A is applied to a bleeding wound, chitosan derivative (e.g., chitosan lactate and/or chitosan lactyl) stimulates and adheres to platelets and red blood cells. These cells concentrate at the wound/bandage interface because of the positive charge of chitosan and porosity of the bandage. In effect, the fibrous article comprising the bandage filters red blood cells and platelets. Blood fluids containing soluble proteins penetrate into the fibrous bulk layers and encounter the silica, thereby initiating the intrinsic cascade.

A clot initiated by multiple procoagulants—an intrinsic cascade initiator and a platelet stimulator—results in the formation of an extensive network of fibrin that includes platelets and red blood cells. The resulting clot forms rapidly and is robust. Furthermore, the hydroscopic silica dehydrates the blood and concentrates the clotting factors near the wound interface. This further facilitates the clotting process. Having a flexible, porous article with a high surface area and multiple procoagulant and/or therapeutic agents stimulates a robust clot and is conformable to most or all wound geometries resulting in an improved hemostatic bandage.

An alternative embodiment of the chitosan-coated base fibrous article, with a different filler formulation that combines fumed silica with precipitated silica (fibrous article type B), was made for use in trials 11-14 and in an extensive in-vivo animal trial described in Example 10. Example 10 is a controlled, repetitive trial demonstrating the superior hemostatic performance obtained with a modified base fibrous article (FIG. 10A) when compared to a commercially available chitosan-based HemCon® bandage (FIG. 10B) and a standard surgical laparotomy (LAP) sponge (FIG. 10C). Table 1 below summarizes the trial results, and FIG. 10D shows distributions of the experimental data. The trial results show that wounds treated with fibrous article type B bled less and the volume of resuscitation fluids required to restore pre-injury blood pressure was also less compared to the HemCon® bandage and laparotomy sponges.

EXAMPLE 1

In this example, a mixture was made containing 92% by weight powdered chitosan and 8% by weight ultrahigh molecular weight polyethylene (UHMWPE, Ticona 4120). About 33% by weight SOY CLEAR™ processing oil was added to the mixture. The mixture was fed to a feed port of a 27 mm co-rotating twin screw extruder. SOY CLEAR™ processing oil was also fed into the feed port in an amount that raised the total process oil content to about 80% by weight of the mixture. The mixture was heated to about 180° C. in the extruder. The resulting gel extrudate was fed through a melt blown die, and the melt blown strands were collected upon a moving porous collector belt to form a continuous nonwoven web. Sheet samples were cut from the nonwoven configuration of macrofibers, and the processing oil was extracted with HFE-7200 solvent supplied by 3M under the trade name Novec™. The sheets can be used as a bandage for covering a bleeding wound.

EXAMPLE 2

Figure 11:
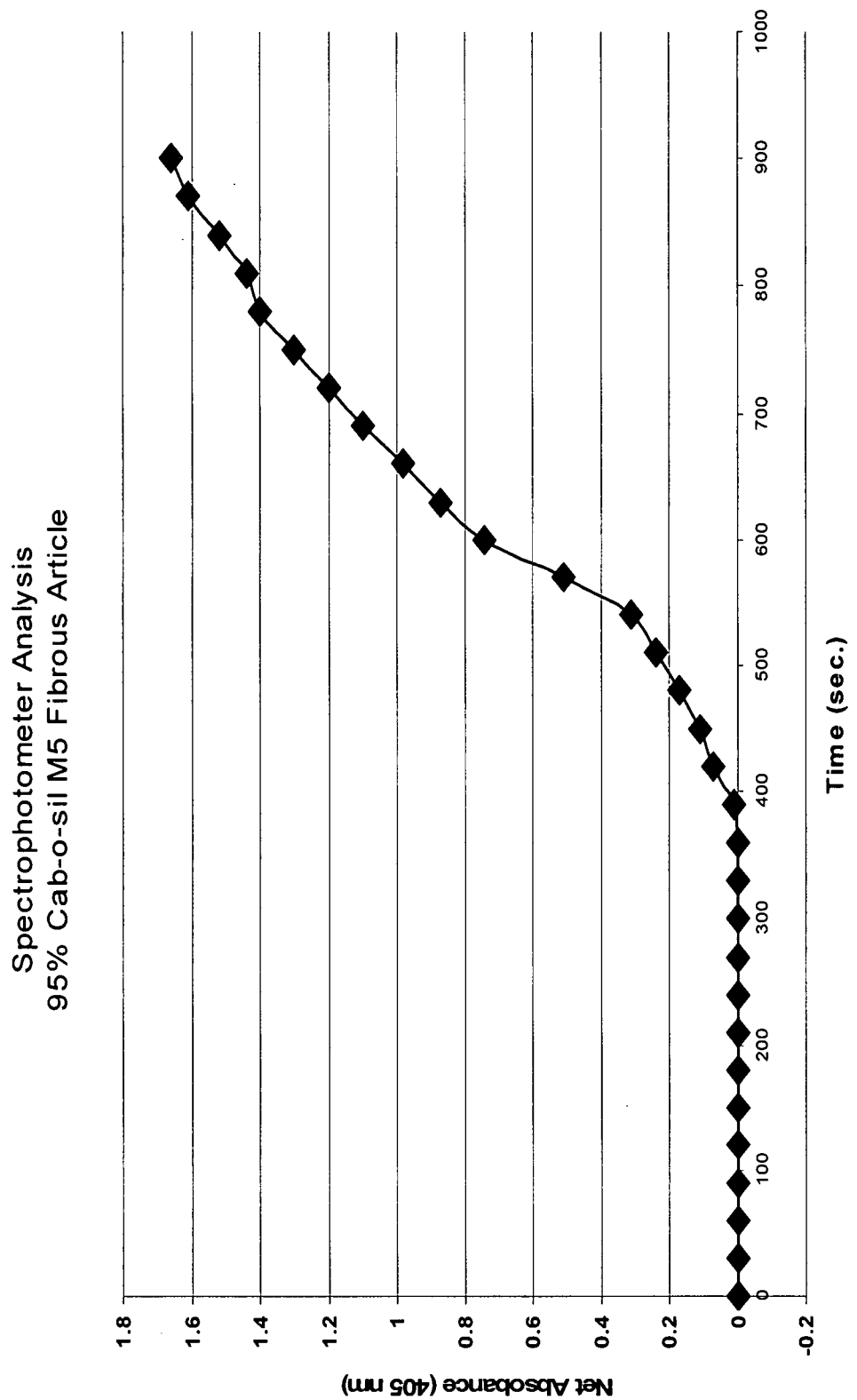
FIG. 11 is a graph of results of a spectrophotometer assay of an article of filled polymeric macrofibers that initiate and sustain fibrin formation in human plasma.

In this example, a modified Activated Prothrombin Time (aPTT) spectrophotometric assay was performed on a sample of fibrous article type A to determine the in vitro clot initiation properties of this material. The sample was cut into a 1 cm×1 cm square and placed at the bottom of 1 ml disposable spectrophotometer cuvette. The cuvette containing the sample was placed in a temperature-controlled spectrophotometer (Beckman Instruments, Fullerton, Calif.). Then, 1.5 ml of standardized FACT human plasma (George King Biomedical, Overland Park, Kans.) was introduced into the cuvette. After the spectrophotometer was blanked at 405 nm, 136.4 µl of 0.2 M calcium chloride solution was added to the cuvette and the absorbance was measured at 405 nm. FIG. 11 shows the change in absorbance with time. The rise in absorbance indicates fibrin formation, suggesting that the material would initiate a blood clot in vivo.

EXAMPLE 3

Figure 12:
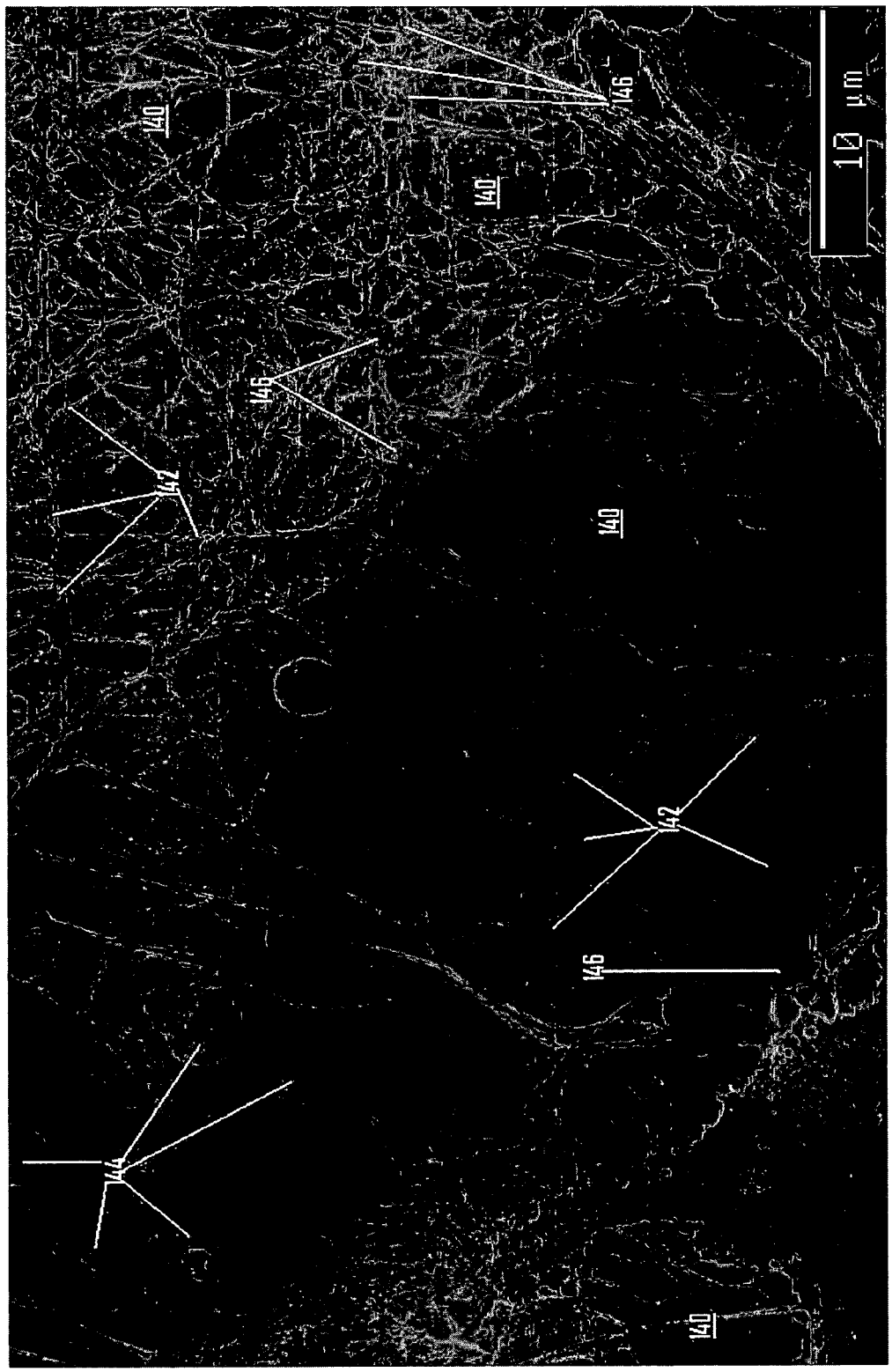
FIG. 12 is a SEM image showing an article of filled polymeric macrofibers exposed to blood in the cavity of a coagulopathic domestic swine.
Figure 13:
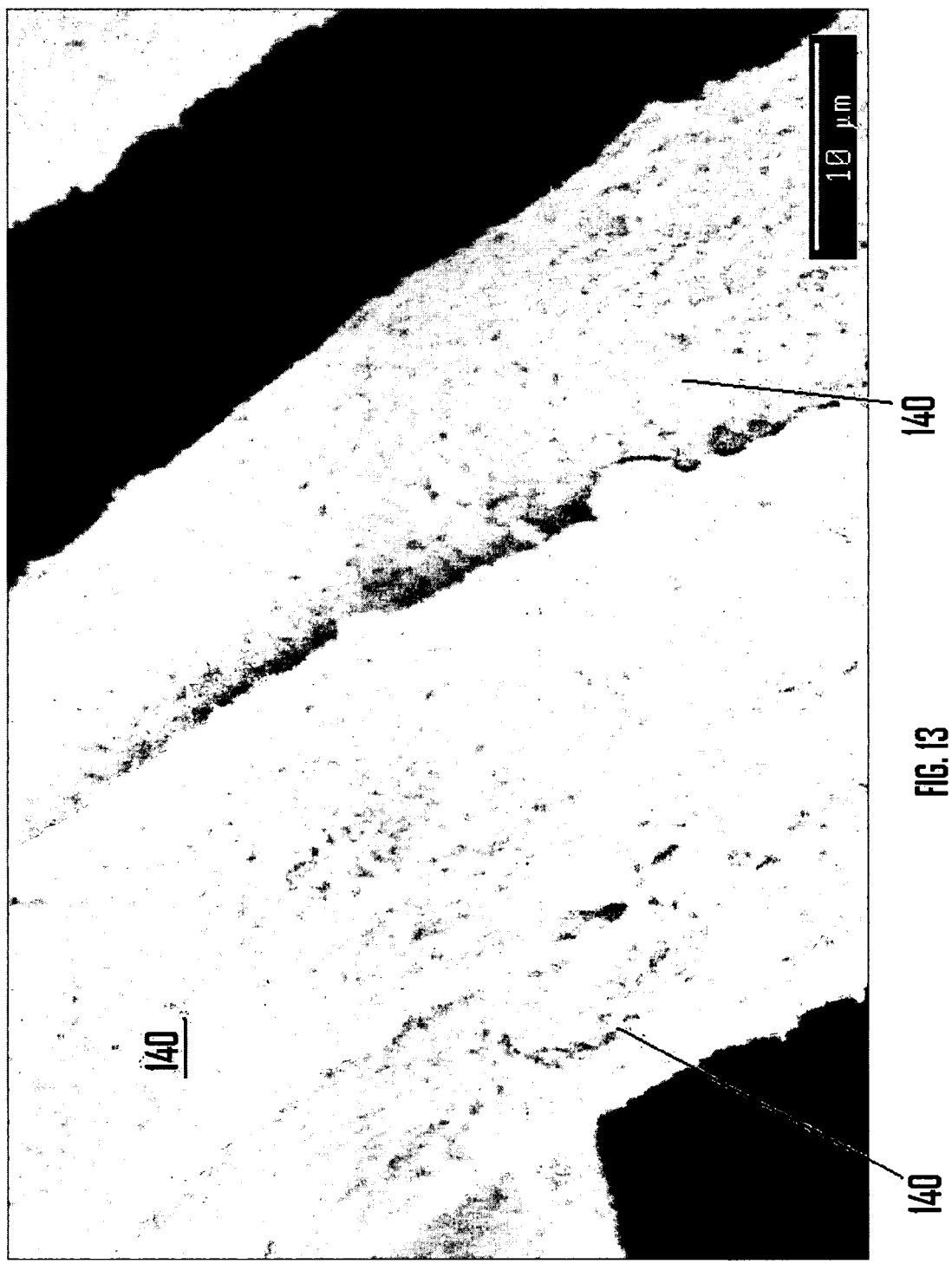
FIG. 13 is a SEM image showing an article of polymeric macrofibers filled with Cab-o-sil M5 fumed silica.

In this example, a 10 cm×10 cm×0.3 cm sample of fibrous article type A was saturated with blood by placing the sample in the cavity of a coagulopathic domestic swine. A portion of this sample was prepared for SEM analysis and is shown at 2000× magnification in FIG. 12. An unexposed sample is shown in FIG. 13. Each of FIGS. 12 and 13 shows multiple macrofibers 140, similar to those shown in FIG. 5. Comparison of these two images reveals that fibrin 142 (a spider web-like structure containing red blood cells 144 and platelets 146 on the surface of the fibrous article) is evident in the exposed sample of FIG. 12, indicating the formation of a blood clot.

Examples 4 and 5 presented below entailed the use of Yorkshire swine, a type of domestic swine, because domestic swine are well established as a standard model for the study of hemorrhage in human beings. These two examples verify, therefore, the efficacy of the articles of filled polymeric macrofibers in reducing blood flow from a wound site. The swine were made coagulopathic and prepared for a midline laparotomy and subsequent grade 5 liver injury in accordance with methods similar to those discussed by Schreiber et. al. *Journal of Trauma*, 53:252-259, 2002.

EXAMPLE 4

In this example, bandages were fabricated measuring approximately 10 cm×10 cm×0.3 cm made of fibrous article type A. A 28 kg swine was made coagulopathic by removing approximately 60% of the calculated blood volume and replacing the lost blood volume with an equivalent volume of a 5% albumin solution. Hypothermia was induced by reducing the swine's body temperature from 37° C. to 33° C. Next, a grade 5 liver injury was induced in the center of the liver using a liver clamp. The wound was allowed to bleed freely for approximately 30 seconds. One article was placed inside the wound cavity, followed by a second article placed on top of the wound cavity, and finally a third article was placed on the bottom side of the wound cavity, thereby completely covering the wound site. Pressure was applied to the top, bottom, and side surfaces of the liver at or near the wound site for one minute, at which time the pressure on the top and bottom surfaces was released. The side-to-side pressure continued for one additional minute.

Upon release of the pressure, a significant reduction in blood flow was observed from the wound site. An additional piece of the article was placed on each of the top of the wound and the bottom of the wound, covering the original materials. Pressure was again applied for one minute top to bottom and continued on the sides for one minute after the top to bottom pressure was released. No blood flow was observed from the wound site for approximately 15 minutes. In a post-mortem inspection, the liver was removed. Blood clots were observed both on the liver and on the article. The top and bottom articles were also adhered to the exterior of liver surrounding the wound.

EXAMPLE 5

In this example, fibrous article type A was lofted using a dry argon jet in a circular motion, achieving a thickness of 0.5 cm. A 35.5 kg swine was prepared as described above in Example 4. Unobstructed blood flow was allowed for approximately 30 seconds after a grade 5 liver injury was induced. Pressure was applied on the top and the bottom of the injury and to the both sides of the injury in a similar manner to that described above in Example 4. Pressure was released from the top and bottom after one minute but continued for one additional minute on the sides. After the pressure was released, no blood flow was observed from the injury for approximately 25 minutes. In a post-mortem inspection, the liver was removed with the articles intact. Blood clots were observed on the liver and on the articles. The top and bottom articles were adhered to the exterior of liver surrounding the wound.

EXAMPLE 6

In this example, fibrous article type A was spray-coated on both sides with a 1% chitosan lactate solution, dried in a convection oven at 240° F. for 1 hour, and lofted to 0.5 cm thick. The articles gained on average 0.7% by weight. In this example, a 34.6 kg swine was prepared as described above in Example 4, except that the subject was not made coagulopathic, hypothermia was not induced, and no blood was removed prior to injury. Free blood flow from the wound site was allowed for five minutes after a grade 5 liver injury was induced. The coated fibrous articles were placed on the wound, and pressure was applied for five minutes on top, bottom, and side surfaces of the liver as described in Examples 4 and 5. After the pressure was released, no blood flow was observed for one hour, at which time the study was ended. During the hour after the pressure was released, a pre-injury baseline mean average blood pressure was achieved and maintained by administering lactated Ringer's resuscitation fluids.

EXAMPLE 7

In this example, fibrous article type A was spray-coated on both sides with a 1% chitosan lactate solution, dried in a convection oven at 220° F. for 1 hour, and lofted to 0.5 cm thick. The articles gained on average 0.7% by weight. A 34.2 kg swine was prepared as described above in Example 6. Free blood flow from the wound site was allowed for 30 seconds, as opposed to the five-minute bleed time discussed in Example 6. A shorter post-injury bleed time poses more of a challenge to achieving hemostasis because of higher bleeding rates and higher blood pressure. The coated fibrous articles were placed on the wound, and pressure was applied to the top, bottom, and side surfaces of the liver as described above in Examples 4, 5, and 6. After the pressure was released, a minor amount of bleeding was observed from the wound. As described in Example 6, a pre-liver injury mean average baseline blood pressure was achieved and maintained for one hour, at which time the study was ended. Total blood loss after the application of the fibrous article was 336 ml.

EXAMPLE 8

In this example, fibrous article type A was spray-coated on both sides with a 2% chitosan lactate solution for approximately 20 seconds on each side, dried in a convection oven at 240° F. for 1 hour, and lofted to 0.5 cm thick. The average weight gain after spraying and then drying the samples was 2.1%. In this example, a swine was prepared as described above in Example 6. As in Example 7, unobstructed blood flow was allowed for 30 seconds, at which time the coated fibrous articles were placed in the wound and held for five minutes as described in Examples 4, 5, and 6. After the five-minute hold period, the pressure was released from the bandages. No bleeding was observed coming from the wound site. As described in Example 6, a pre-liver injury mean average baseline blood pressure was achieved and maintained for one hour, at which time the study was ended.

EXAMPLE 9

In this example, one group of fibrous article type A was sprayed with a 2% chitosan lactate solution for approximately 20 seconds on each side and then dried for one hour in a convection oven at 240° F. The average weight gain after spray-coating and then drying the articles was 2.6%.

A second group of articles used in this example was comprised of fibrous article type A, except that this secondary group was prepared by spray-coating with a 2% chitosan solution dissolved in 2% lactic acid for 25 seconds on each side. The chitosan used to make this solution was Chitoclear FG 90, obtained from Primex EHF of Siglufiordur, Iceland. After spray-coating, the articles were dried at 240° F. for approximately one hour and attained an average weight gain of 3.2%.

In this example, a swine was prepared as described above in Example 6 (i.e., non-coagulopathic and non-hypothermic). As in Examples 7 and 8, free blood flow was allowed for 30 seconds, at which time the first group of coated fibrous articles was placed in the wound and held for 5 minutes as described in Examples 4, 5, and 6. After the five-minute hold period, the pressure was released from the articles. As described in Example 6, a pre-liver injury mean average baseline blood pressure was achieved and maintained for one hour by administering lactated Ringer's solution. No bleeding was observed from the wound for one hour after application of the articles, at which time the animal was made coagulopathic and hypothermic by methods described by Schreiber et. al., *Journal of Trauma*, 53:252-259, 2002. The animal was allowed to stabilize, and a pre-injury mean blood pressure was maintained by administering lactated Ringer's solution. No bleeding from the wound site was observed for approximately two hours after starting the procedure to induce a coagulopathic and hypothermic state. After this time, the first set of articles was removed from the wound and the wound was stimulated digitally to cause bleeding. Free blood flow was allowed for approximately 30 seconds, at which time the second group of articles was placed on the wound and pressure was applied for five minutes as described in Examples 4, 5, and 6. A pre-injury mean base line blood pressure was maintained as described above. No blood loss was observed from the wound for the 30 minutes after pressure was released from these articles, at which time the study was ended.

EXAMPLE 10

In this example, a controlled trial was run, using 50 fibrous articles prepared with a different silica formulation. Instead of fibrous article type A, a different combination (fibrous article type B) of 49% Cab-o-sil M5 fumed silica and 45% Hi-Sil SBG precipitated silica was substituted, with 6% Ticona 4120 UHMW PE. Each article was spray-coated on each side with 10 ml of 2% Chitoclear FG 90 dissolved in 2% lactic acid solution and then dried in a convection oven at 220° F. for 1 hour. The finished fibrous articles were placed five each in mylar bags and sealed immediately after weighing.

30 Yorkshire swine, ranging in weight from 30 kg to 52 kg were randomized and placed into three groups to compare the performance of three different wound dressings for hemostatic efficacy in a potentially lethal groin injury model: One laporatomy (LAP) sponge commonly used in surgery (18 cm×18 cm, folded), two HemCon® bandages, and five fibrous articles of type B (10 cm×10 cm) were tested. The number of dressings applied in each case was determined according to its therapeutic equivalence as judged by a surgeon. Each swine was anesthetized using 8 mg/Kg of Telazol 1M and maintained using 1%-3% isofluorane, adjusted for reflexes, and inhaled in 50% oxygen. Femoral vessels were exposed, and overlying abductor muscles were retracted. The groin was lacerated to include the overlying abductor muscles and complete transection of the femoral artery and vein. Bleeding was allowed for 30 seconds, at which time the dressing was applied. LAP sponges were placed over each dressing, and five minutes of direct pressure was applied in each case. Upon release of the pressure, resuscitation with lactate Ringer's solution was initiated at a rate of 165 ml/min to a per-injury baseline mean arterial pressure (MAP). The wounds were observed, and failure was determined if blood pooled around the dressing and spilled out of the wound cavity. Each study was concluded at the time of death or after two hours. In this study, the fibrous articles of type B stopped the bleeding in 9 of out 10 evaluations, while the LAP sponges and HemCon® bandages stopped the bleeding 5 out of 10 and 2 out of 10 times, respectively.

Table 1 presents detailed performance data comparing fibrous article type B against prior art commercial dressings. In this study of 30 Yorkshire swine, fibrous article type B demonstrated superior performance for each of the following criteria: hemostasis (bleeding stopped), blood loss, and volume of resuscitation fluid. For each trial, a dressing was determined to have stopped the bleeding if, upon release of direct pressure, blood did not flow over the edges of the injury cavity. Blood loss before 30 seconds was the blood loss resulting from the injury prior to insertion of the dressing. "Blood loss after insertion" includes blood absorbed into the dressing, blood absorbed into the LAP sponges placed above the test dressing and, in cases in which hemostasis was not achieved, any blood that may have spilled out of the injury cavity. Resuscitation fluids were administered after five minutes of direct pressure and were measured until the end of the study or for a two-hour period.

TABLE 1

Comparison of fibrous article type B against commercial dressings.

| | N (# tested) | Hemo-stasis | Mortality % | Blood Loss after insertion (mls) | Resus. Fluids (mls) |
|---|---|---|---|---|---|
| Fibrous Article B | 10 | 9 | 10% | 638 ± 1690 | 4550 ± 4000 |
| HEMCON® | 10 | 2 | 30% | 1916 ± 2100 | 6630 ± 4850 |
| LAPS | 10 | 5 | 10% | 793 ± 1230 | 6230 ± 4220 |

Figure 10A:
FIGS. 10A, 10B, and 10C are photographs of, respectively, a conformable chitosan-coated base fibrous article, a prior art chitosan material, and a prior art standard surgical laparotomy (LAP) sponge for comparison of conformability when each material is used as a bandage.
Figure 10B:
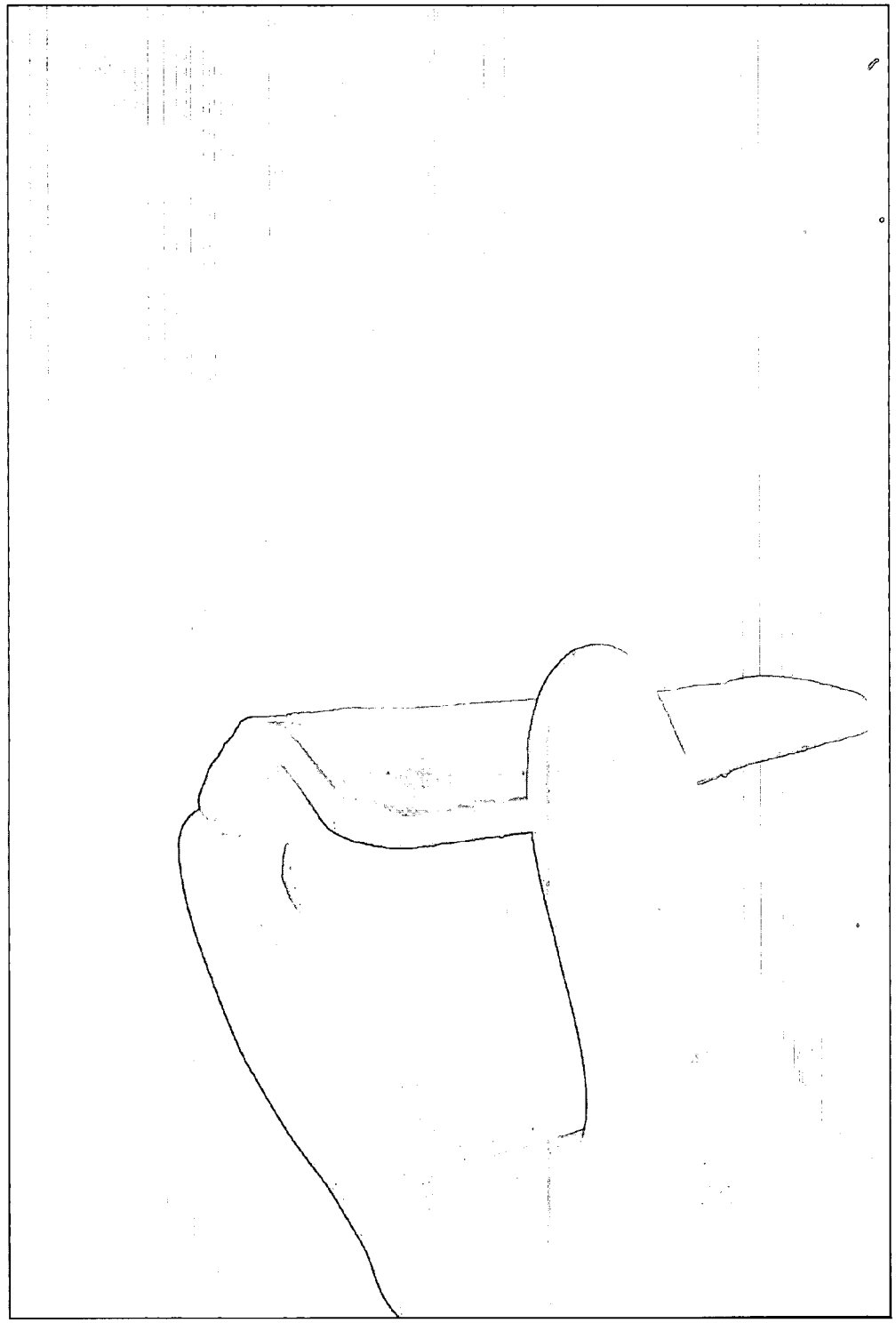
Figure 10C:
Figure 10D:
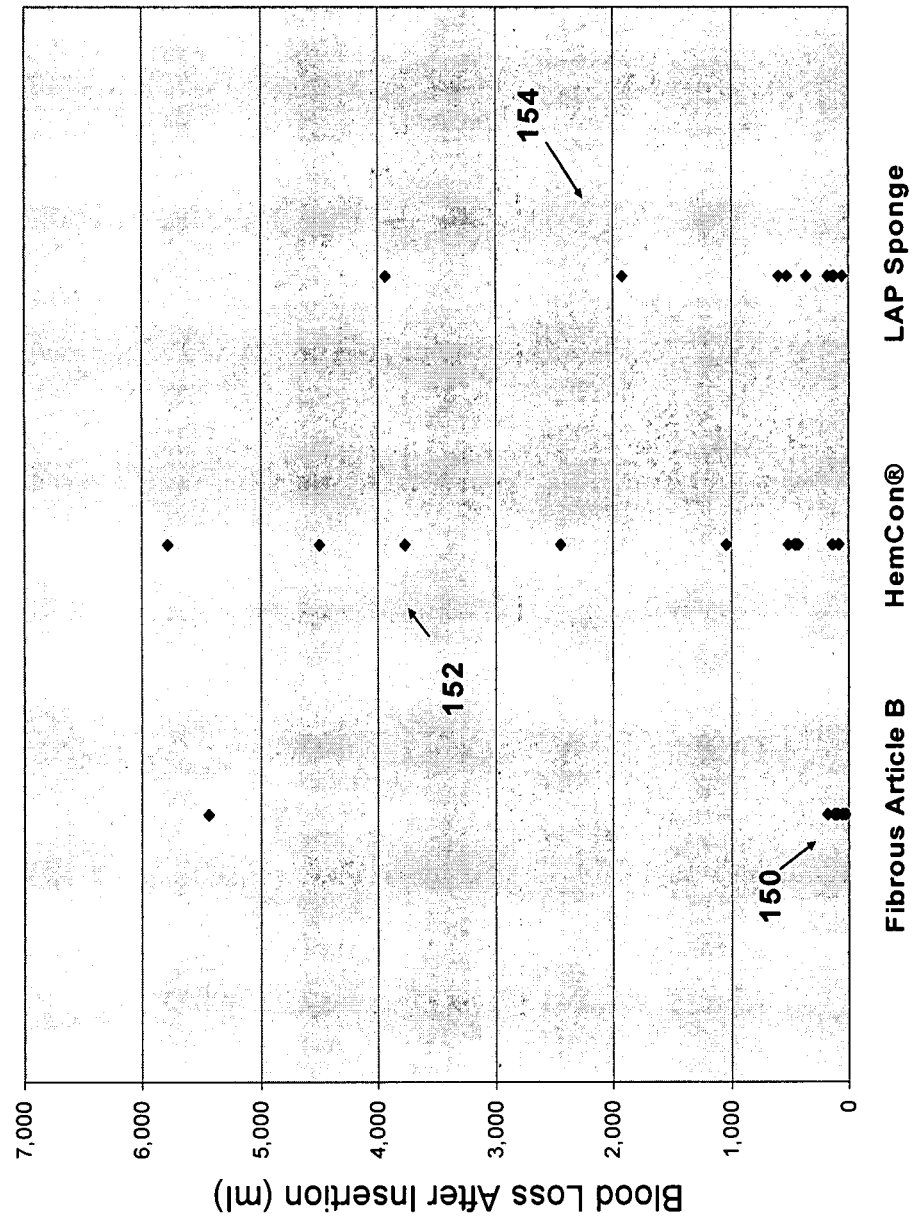
FIG. 10D is a graph of blood loss after dressing insertion during in-vivo experiments comparing the three materials shown in FIGS. 10A-10C.

FIG. 10D shows the blood loss after dressing insertion for 30 trials, 10 trials for each of the test dressings of FIGS. 10A-10C. A narrow distribution 150 of 9 data points demonstrates a relatively low blood loss compared with a wide distribution 152 of data points for the HemCon®D bandage and a wide distribution 154 of data points for the LAP sponges. The commercial dressings of FIGS. 10B and 10C show a higher average, consistent blood loss when compared with that of fibrous article type B.

The favorable results obtained in Example 10 can be understood in light of the unique structure of the composite base fibrous article. The functional filler particles, silica in this case, are not simply adhered to the outside of a binder or fibers or retained by overlapping fibers, as in the prior art examples described above. The functional filler particles are held in place within individual macrofibers with a minimal amount of binder. Since the functional filler is a large component of the macrofiber and has a structure that separates individual particles or agglomerates of particles within the macrofiber without being blinded by the binder, the macrofiber is therefore porous and presents a high surface area of the functional filler particles.

Articles composed of filled macrofibers have, therefore, inter-fiber spaces that allow bulk penetration of a fluid into the article and intra-fiber porosity that allows penetration into individual fibers. The manifest advantages of this architecture are the very high ratio of procoagulant and/or therapeutic agents to binder, the high available surface area of the procoagulant and/or therapeutic agents, the retention of the functional filler particles when the article is exposed to a moving fluid, high mass transfer rates between the article and adsorbates, and the flexibility of the article. These properties are all important and beneficial for a hemostatic device.

The porous macrofibers within the article facilitate rapid mass transfer with a fluid, such as blood. The article allows rapid adsorption of components of the blood onto the surface of the procoagulant filler, as in the procoagulant application or dissolution of therapeutic filler into a fluid, as in a drug delivery application. Additionally, the very efficient use of binder material in a porous network of fibers allows for a high degree of flexibility, whereas in other methods, filled materials become brittle as loading levels of fillers increase.

Thus, in the case of fibrous article type B, the property of a high filler-to-binder ratio maximizes the quantity of intrinsic clot cascade initiator presented to the wound in a flexible dressing. Unlike prior art approaches that rely on only one clotting mechanism (e.g., platelet stimulation, without benefit of intrinsic cascade initiators), the approach of the present inventors is believed to combine clotting mechanisms: intrinsic cascade initiation, platelet stimulation, and red blood cell agglutination. Additionally, as the blood is absorbed into the material, dehydration of the plasma, which concentrates the clotting factors, and filtration of red blood cells and platelets contribute to clotting. One or both of platelet stimulation and red blood cell agglutination take place in response to introduction of procoagulants that do not initiate the intrinsic clotting cascade by themselves, such as, for example, chitosan or chitosan derivative. In preferred embodiments, a silica filler (functioning as an intrinsic cascade initiator) of and a chitosan coating (stimulating one or both of platelet activation and red blood cell agglutination) on fibrous article type B cooperate to accelerate hemostasis, resulting in superior performance observed in-vivo. Supplementing the coating with a calcium compound, for example, $CaCl_2$, $CaO$, or $CaCO_3$ further improves the procoagulant effect of the coating. Preliminary experiments suggest that ethanol may also improve performance of the coated material.

EXAMPLE 11

In this example, surface areas of various materials with and without coatings were characterized, under the assumption that high surface area is a desirable property for effective hemostasis. Aspects of blood clotting entail the interaction of surface initiators with blood. A five point Brunauer-Emmett-Teller (BET) nitrogen adsorption method using a Micormetics ASAP 2020 Accelerated Surface Area and Porosimetry Analyzer was performed to obtain surface area measurements of fibrous articles of types A and B. The samples were degassed at 40° F. before the analysis. Table 2 presents the surface area measurements obtained for fibrous articles of types A and B in comparison with commercial dressings.

According to data summarized in Table 2, the surface areas for coated and uncoated fibrous articles, which measured about 100 $m^2/g$, are two orders of magnitude larger than the surface areas of either the LAP sponges or the HemCon® bandage, which measured about 1 $m^2/g$ or less. These measurements suggest to the inventors that a fibrous article having a structured procoagulant surface area of greater than 10 $m^2/g$ provides effective hemostasis properties. Because it is a chitosan-based product, the HemCon® bandage was tested as received without a spray-coating of chitosan lactate.

TABLE 2

BET surface area comparisons of coated and uncoated fibrous article A and B with commercial dressings: HemCon ®, and LAP sponges.

| | Filler | Spray-Coating | Surface Area ($m^2$/gram) |
|---|---|---|---|
| Fibrous article type A | 95% fumed silica | none | 148.3 |
| Fibrous article type A | 95% fumed silica | chitosan lactate | 80.7 |
| Fibrous article type B | 49% fumed silica 45% precipitated silica | none | 135.62 |
| Fibrous article type B | 49% fumed silica 45% precipitated silica | chitosan lactate | 113.44 |
| A-Med Laparotomy sponge | as received | as received | 0.89 |
| A-Med Laparotomy sponge | as received | chitosan lactate | 0.54 |
| HemCon ® | as received | none | 1.16 |

EXAMPLE 12

In this example, the effects of temperature and bake time during the preparation of fibrous article type B samples were investigated. Samples similar to those used in Examples 10 and 11 were prepared with drying times and temperatures as indicated in Table 3A. The fibrous articles heated for 15 minutes at 220° F. were also treated with isopropyl alcohol to remove any residual lactic acid before being dried. All of the samples in Table 3A were tested using a second groin injury inflicted on a Yorkshire swine after it had sustained a primary groin injury, been treated with one of the three products described in Example 10, and stabilized for at least 2 hours. The secondary groin injury was inflicted in the opposite groin from that of the primary injury. The secondary injury, dressing application, direct pressure hold time, and resuscitation protocol were the same as those described in Example 10.

TABLE 3A

Performance comparison of Fibrous Articles prepared under different drying conditions.

| Temperature (° F.) | Time (min.) | Hemostat Performance | Range of Motion Test | MAP |
|---|---|---|---|---|
| 220 | 90 | Pass | Pass | 70 |
| 310 | 15 | Pass | Pass | 85 |
| 310 | 15 | Pass | Pass | 67 |
| 220 | 15 | Fail | no test | 69 |
| 220 | 15 | Fail | no test | 80 |
| 220 | 15 | Pass | Fail | 90 |

The "MAP" column of Table 3A indicates the mean arterial pressure attained after resuscitation fluids were administered. The "Hemostat Performance" column indicates whether bleeding was observed to pool and spill over the wound cavity. "Fail" means that blood did spill over the wound cavity, and "Pass" indicates that blood did not spill over the edges of the wound cavity. As indicated in this column, the swine treated with fibrous articles heated at 220° F. for 90 minutes or fibrous articles heated at 310° F. for 15 minutes were resuscitated to the Mean Arterial Pressure (MAP) presented in Table 3A without any blood loss from the wound. Two of the three trials using fibrous articles heated for 15 minutes at 220° F. failed at the MAPs indicated in Table 3A.

The column labeled "Range of Motion Test" in Table 3A indicates whether significant bleeding resulted from manipulating several times through a normal range of motion the leg on the side of the secondary groin injury. The fibrous article heated to 220° F. for 90 minutes did not show significant blood loss as a result of this motion, and similar results were seen in both trials performed with articles dried at 310° F. for 15 minutes. Fibrous articles dried at 220° F. for 15 minutes either failed to stop bleeding or failed the range of motion test. These evaluations indicate that drying fibrous articles spray-coated with chitosan lactate solution at higher temperatures and/or for longer times is beneficial in achieving hemostasis.

This trend in hemostatic performance versus drying time and/or temperature can be correlated to the volume of a basic solution used to neutralize the pH of a 1-gram sample of fibrous article. Table 3B presents the titration volume of 0.01 M potassium hydroxide (KOH) required to change a solution of 50 ml of deionized water and 5 drops of phenyl red indicator dye from yellow to pink after soaking a sample of fibrous article in the solution. It is known that the salt formed by de-acetylated chitosan and an organic acid, for example, chitosan lactate when de-acetylated chitosan is treated with lactic acid, can be titrated with a basic solution. Heating the chitosan salt is known to convert the salt to chitosan lactyl. Chitosan lactyl cannot be titrated with a basic solution. Table 3B indicates the amount of each type of chitosan-lactate or chitosan condensate from the salt. Table 3B indicates that higher drying temperature and/or longer drying time converts chitosan lactate to chitosan lactyl. The data in Tables 3A suggest that the articles with more conversion of chitosan lactate to chitosan lactyl are more efficacious for hemostatis. The fibrous articles prepared in Example 12 each constitute a chitosan condensate structured in a high surface area configuration, which results from the silica's functioning as a high surface area substrate for the chitosan condensate.

TABLE 3B

Titration volume comparison of coated fibrous article samples prepared under different drying conditions.

| Temperature (° F.) | Time (min.) | Titration Vol. (ml of 0.01M KOH/gram) |
|---|---|---|
| 220 | 90 | 2.5 |
| 310 | 15 | 0.7 |
| 220 | 15 | 11.4 |

EXAMPLE 13

In this example, the effect on hemostasis performance of adding a calcium compound to the chitosan lactate coating was determined. An article of filled polymeric macrofiber was prepared the same way as in Example 10, except that a sample 1 was spray-coated with a 2% chitosan lactic solution that was first diluted 4:1 parts-by-volume with 0.025 M $CaCl_2$ solution. A sample 2 was prepared using an identical solution as described in Example 10, containing no $CaCl_2$ solution.

A Yorkshire swine was prepared as in Example 4 and made hypothermic and coagulopathic. Achieving hemostasis in splenetic injuries is known to be difficult, especially under coagulopathic and hypothermic circumstances. The spleen was exposed, and two 0.5 cm cuts were made approximately 2 cm apart using a scalpel. Both spleen injuries were allowed to bleed freely for 30 seconds, at which time a 1 cm×1 cm piece of sample 1 was placed on one wound and a similar sized piece of sample 2 was placed on the other wound. Direct pressure was applied to each wound for 5 minutes, at which time the pressure was removed and the samples were observed. Sample 1 containing the $CaCl_2$ showed that a small amount of blood had soaked into the center, but no further bleeding from the sample was observed. Blood soaked through sample 2, and bleeding was not stopped.

EXAMPLE 14

In this example, a fibrous article was prepared in a similar manner as fibrous article type B was prepared, and then was segmented by hand-shredding the material into a mixture of very short strands, granules, and powder. To test the efficacy of this segmented form of hemostatic material, a mid-line incision was made in an anesthetized Yorkshire swine to expose the spleen. A 20 mm circular punch was used to make an approximately 1 mm deep incision in the spleen. Scissors were then used to remove the tissue in the circular incision. Less than 0.5 gram of shredded fibrous material was placed over the wound, and pressure was repeatedly applied 3 to 4 times for approximately 15 seconds each time. After each application of pressure, the wound was observed for bleeding. After the fourth application, it was observed that bleeding from the covered wound had completely stopped. After approximately 20 minutes of observation with no further bleeding, the segmented fibrous material, having absorbed enough fluid that the strands, granules, and particles held together in a conglomerate, was forcibly removed in one piece. Bleeding resumed in a similar way as before the fibrous article was applied. It was concluded that addition of a sorbent polymer to the segmented article may desirably provide more pressure and absorb water, thereby further dehydrating the wound and decreasing the time to achieve hemostasis.

EXAMPLE 15

In this example, filler composition, lofting, exposure to electron beam radiation, bandage construction, bake time, and temperature and fibrous article moisture level were investigated. Moisture content is significant because it affects the flexibility of the article. Four different fibrous article types were evaluated in lethal groin injuries on Yorkshire Swine. The injuries were performed in a similar manner to that described in Example 10, except that both hind groins were used. The injury and insertion process was first performed in the right hind groin, and then after the 30 minutes of observation, the injury and insertion process was repeated in the left hind groin.

As described in Example 10, the femoral artery and vein were completely transected, and the wound was allowed to bleed freely for 30 seconds. Following the bleed time, four 10 cm×10 cm samples of the fibrous article type were inserted into the wound and a laparotomy sponge was placed over the wound. Direct pressure was the applied for 5 minutes. Upon release of pressure, the wound was observed for 30 minutes. Next, the process was repeated in the left hind groin using the fresh bandages of the same type. Each fibrous article type was evaluated in two swine for a total of four groin injuries for each article type.

Table 4 describes each fibrous article type used in this example. Fibrous article types C, D, E, and F were each coated with a 2% chitosan lactate solution as described in Example 9. Fibrous article type C was prepared in a similar manner to that described for fibrous article type B, except that article type C was exposed to 25 kGy of electron beam radiation after packaging. Fibrous article type D was also prepared in a similar manner to that described for fibrous article type B, except that each of the 10 cm×10 cm samples was removed from its package, sprayed with de-ionized water using an air brush sprayer to achieve approximately 5% weight gain, and then repackaged. Fibrous article type E was made using a filler composition of 80% precipitated silica and 12% fumed silica by weight. Article type E was not lofted and was constructed in three thin layers before spray coating with a similar chitosan lactate solution to that used in article types C and D. After drying in a convection oven at 220° F. for 60 minutes, each 10 cm×10 cm sample of type E was sprayed with de-ionized water using an air brush sprayer to achieve an approximate weight gain of 11%. A moisture content of up to about 15% by weight would provide the desired flexibility to the article. Finally, fibrous article type F was prepared in a similar manner to that performed for article type E, except that it was dried at 265° F. for 30 minutes before receiving the water spray and then being packaged. All 10 cm×10 cm samples of each article type were similar in weight.

Hemostasis was achieved in each of the 16 evaluations. Blood loss after insertion was estimated to be less than 60 ml for each injury.

TABLE 4

Description of fibrous article types C, D, E, and F

| Fibrous Article Type | Filler | Lofting (Y/N) | Construction | Bake Temp/Time (° F./min.) | Water Spray Weight Gain (%) |
|---|---|---|---|---|---|
| C | 49% fumed silica 45% precipitated silica | Y | 1 Layer | 220/60 | 0 (no spray) |
| D | 49% fumed silica 45% precipitated silica | Y | 1 Layer | 220/60 | 5 |
| E | 12% fumed silica 80% precipitated silica | N | 3 Layers | 220/60 | 11 |

TABLE 4-continued

Description of fibrous article types C, D, E, and F

| Fibrous Article Type | Filler | Lofting (Y/N) | Construction | Bake Temp/Time (° F./min.) | Water Spray Weight Gain (%) |
|---|---|---|---|---|---|
| F | 12% fumed silica 80% precipitated silica | N | 3 Layers | 265/30 | 11 |

The fibrous articles described in the examples presented can be included in sterile packaging to form a therapeutic dressing kit. The kit may also include fasteners adapted to affix the fibrous articles to mammalian subjects.

It will be obvious to those having skill in the art that many changes may be made to the details of the above-described embodiments without departing from the underlying principles of the invention. The scope of the present invention should, therefore, be determined only by the following claims.

The invention claimed is:

1. A composite nonwoven article of filled polymeric macrofibers for use as a therapeutic dressing in the treatment of a wound site of a mammalian subject, comprising:
    multiple networks of microfibers, each of the multiple networks of microfibers including multiple submicron-diameter polymeric microfibers having diameters of between about 50 nm and about 500 nm and containing and binding therapeutic agent particles in a configuration that presents a large available surface area of therapeutic agent with insubstantial blockage by the microfibers, the networks of microfibers exhibiting intra-fiber porosity produced by free spaces around the therapeutic agent particles and the microfibers; and
    multiple micron-diameter porous polymeric macrofibers, each of the multiple polymeric macrofibers having a diameter of greater than 10 μm and less than about 500 μm presenting a structured architecture formed of one of the multiple networks of microfibers containing and binding therapeutic agent particles, the macrofibers randomly oriented to form a composite nonwoven article exhibiting inter-fiber porosity around the macrofibers, the randomly oriented macrofibers of the composite nonwoven article exhibiting intra- and inter-fiber porosity at submicron and micron scales with appreciable free space around the therapeutic agent particles contained and bound by the network of microfibers so that blood from the wound site penetrates the composite nonwoven article of filled polymeric macrofibers to come in contact with a substantial amount of the therapeutic agent and thereby stimulate a therapeutic response in the mammalian subject.

2. The article of claim 1, in which the therapeutic agent particles include a procoagulant and the stimulation of a therapeutic response includes promotion of blood clot formation.

3. The article of claim 1, in which the therapeutic agent particles include a filler material that contributes to the structured architecture presented by the multiple polymeric macrofibers.

4. The article of claim 3, in which the filler material includes silica and the therapeutic agent particles include chitosan.

5. The article of claim 4, in which the chitosan is suffused or coated on the silica.

6. The article of claim 4, in which the chitosan is in a condensed form on the silica.

7. The article of claim 1, in which the therapeutic agent particles include one or both of a procoagulant that functions as an intrinsic cascade initiator and a procoagulant that contributes to coagulation at least in part by a mechanism other than intrinsic cascade initiation.

8. The article of claim 7, in which the therapeutic agent particles are selected from the group consisting of silica, chitosan, zeolite, absorbent polymers, polysaccharides, chitin, derivatives of chitosan and chitin, starch, kaolin, celite, alum, thrombin, fibrinogen, fibrin, alginate, recombinant factor VIIa, collagen, diatomaceous earth, carbon, von Willebrand factor, fibronectin, vitronectin, thromboxane A2, thrombopoietin, intracellular adhesion molecule (ICAM)-1 and -2, vascular cell adhesion molecule (VCAM), aggretin, adenosine-di-phosphate (ADP), Ristocetin, and mixtures of them.

9. The article of claim 7, in which the procoagulant functioning as an intrinsic cascade initiator includes silica.

10. The article of claim 7, in which the procoagulant contributing at least in part to a mechanism other than intrinsic cascade initiation entails one or both of red blood cell agglutination and platelet stimulation.

11. The article of claim 7, in which the procoagulant contributing at least in part to a mechanism other than intrinsic cascade initiation includes chitosan or chitosan derivative.

12. The article of claim 7, in which the procoagulant contributing at least in part to a mechanism other than intrinsic cascade initiation is coated or suffused on the multiple polymeric macrofibers.

13. The article of claim 12, in which the procoagulant coated or suffused on the multiple polymeric macrofibers further comprises a blood clotting adjuvant that includes alcohol, a calcium compound, or a mixture of them.

14. The article of claim 13, in which the alcohol is selected from a group consisting of isopropyl alcohol and ethanol and the calcium compound is selected from a group consisting of calcium chloride ($CaCl_2$), calcium oxide (CaO), and calcium carbonate ($CaCO_3$).

15. The article of claim 12, in which the procoagulant coated or suffused on the multiple polymeric macrofibers includes chitosan or chitosan derivative.

16. The article of claim 1, in which the multiple polymeric macrofibers have a surface area exceeding a value of about 10 $m^2/g$ as measured by the BET nitrogen absorption technique.

17. The article of claim 1, in which the multiple polymeric macrofibers have a moisture content of less than about 15% by weight.

18. The article of claim 1, in which the multiple polymeric macrofibers are in segmented form of short fibers, granules, or particles and are admixed with a procoagulant or a sorbent polymer.

19. The article of claim 1, in which the multiple polymeric macrofibers further comprise a blood clotting adjuvant that includes calcium chloride ($CaCl_2$), calcium oxide (CaO), calcium carbonate ($CaCO_3$), isopropyl alcohol, ethanol, or a mixture of them.

20. The article of claim 1, in which the multiple polymeric macrofibers include an ultrahigh molecular weight polyolefin.

21. The article of claim 20, in which the ultrahigh molecular weight polyolefin is ultrahigh molecular weight polyethylene.

22. The article of claim 1, in which the therapeutic agent particles comprise no less than about 5% by weight.

23. The article of claim 1, in which the multiple polymeric macrofibers are selected from the group consisting of polyolefins, condensation polymers, vinyl polymers, and natural polymers.

24. The article of claim 1, in which the multiple polymeric macrofibers comprise polyolefin components that include one or more of polypropylene, polyolefin co-polymers, ethylene propylene co-polymers, metallocene polymers, and metallocene polypropylene.

25. The article of claim 1, in which the multiple polymeric macrofibers comprise condensation polymers that include one or more of polyester, polyethylene terephthalate, polyamide, and polyimide.

26. The article of claim 1, in which the multiple polymeric macrofibers comprise vinyl polymers that include one or more of polyvinyl chloride, polystyrene, and co-polymers of polystyrene.

27. The article of claim 1, in which the multiple polymeric macrofibers comprise natural polymers that include one or more of polysaccharides, chitin, chitosan, and cellulosic polymers.

\* \* \* \* \*